(12) United States Patent
Ward

(10) Patent No.: US 11,511,111 B2
(45) Date of Patent: Nov. 29, 2022

(54) SYSTEM AND METHOD FOR GASTRIC ELECTRICAL STIMULATION USING COMPOUND NERVE ACTION POTENTIAL FEEDBACK

(71) Applicant: Purdue Research Foundation, West Lafayette, IN (US)

(72) Inventor: Matthew P. Ward, Zionsville, IN (US)

(73) Assignee: Purdue Research Foundation, West Lafayette, IN (US)

(*) Notice: Subject to any disclaimer, the term of this patent is extended or adjusted under 35 U.S.C. 154(b) by 190 days.

(21) Appl. No.: 17/128,123

(22) Filed: Dec. 20, 2020

(65) Prior Publication Data

US 2021/0260372 A1     Aug. 26, 2021

Related U.S. Application Data

(60) Provisional application No. 62/979,351, filed on Feb. 20, 2020.

(51) Int. Cl.
*A61N 1/00* (2006.01)
*A61N 1/36* (2006.01)
(Continued)

(52) U.S. Cl.
CPC ..... *A61N 1/36007* (2013.01); *A61N 1/36053* (2013.01); *A61N 1/36071* (2013.01);
(Continued)

(58) Field of Classification Search
None
See application file for complete search history.

(56) References Cited

U.S. PATENT DOCUMENTS

2007/0027492 A1* 2/2007 Maschino .......... A61N 1/36053
607/40

OTHER PUBLICATIONS

Ward et al., "A Flexible Platform for Biofeedback-Driven Control and Personalization of Electrical Nerve Stimulation Therapy," in IEEE Transactions on Neural Systems and Rehabilitation Engineering, vol. 23, No. 3, pp. 475-484, May 2015.
(Continued)

*Primary Examiner* — John R Downey
*Assistant Examiner* — Anant A Gupta
(74) *Attorney, Agent, or Firm* — Piroozi-IP, LLC

(57) ABSTRACT

A gastric electric stimulation (GES) system is disclosed which includes a processing system, and at least one of a left vagus nerve sensor (L/R Sensors) and a right vagus nerve sensor coupled to the processing system, the processing system is configured to receive a model which statistically correlates sensed compound nerve action potential (CNAP) parameters measured from at least one of left and right vagus nerves of subjects within a population to feedback surveys of the subjects corresponding to a plurality of gastric symptoms and symptom parameters, receive one or more gastric symptoms of a subject outside of the population (Subject$_{out}$), determine CNAP parameters that correspond to the gastric symptoms with least severity (CNAP$_{min}$), measure CNAP activity of the Subject$_{out}$ from the L/R sensors while modifying GES parameters for the Subject$_{out}$, select the GES parameters that corresponds to the CNAP$_{min}$ (GES$_{out}$), and output the GES$_{out}$.

20 Claims, 17 Drawing Sheets

(51) Int. Cl.

| | | |
|---|---|---|
| *G16H 50/20* | (2018.01) | |
| *G16H 20/30* | (2018.01) | |
| *G16H 50/80* | (2018.01) | |
| *G16H 40/67* | (2018.01) | |
| *G16H 10/20* | (2018.01) | |
| *G16H 50/70* | (2018.01) | |
| *A61N 1/372* | (2006.01) | |

(52) U.S. Cl.
CPC ..... *A61N 1/36132* (2013.01); *A61N 1/36139* (2013.01); *A61N 1/36167* (2013.01); *A61N 1/36171* (2013.01); *A61N 1/36175* (2013.01); *A61N 1/37252* (2013.01); *G16H 10/20* (2018.01); *G16H 20/30* (2018.01); *G16H 40/67* (2018.01); *G16H 50/20* (2018.01); *G16H 50/70* (2018.01); *G16H 50/80* (2018.01)

(56) References Cited

OTHER PUBLICATIONS

Camilleri, "Clinical Practice: Diabetic Gastroparesis," N Engl J Med, vol. 356, No. 8, pp. 820-829, 2007.

Soykan et al., "Demography, clinical characteristics, psychological and abuse profiles, treatment, and long-term follow-up of patients with gastroparesis," Digestive Diseases and Sciences, vol. 43, No. 11, pp. 2398-2404, 1998.

Camilleri et al., "Epidemiology, mechanisms, and management of diabetic gastroparesis," Clinical Gastroenterology and Hepatology, vol. 9, No. 1, pp. 5-12, 2011.

Ward et al., "Gastric Electrical Stimulation of the Antrum Evokes Compound Cervical Vagal Nerve Action Potentials in Rodents," Gastroenterology, vol. 148, No. 4, pp. S507, 2015.

Bilgutay et al., "Gastro-intestinal pacing: A new concept in the treatment of ileus," Annals of Surgery, vol. 158, No. 3, pp. 338-347, 1963.

Bellahsene et al., "Acceleration of gastric emptying with electrical stimulation in a canine model of gastroparesis," Am J Physiol, vol. 262, pp. G826-G834, 1992.

Eagon et al., "Effects of gastric pacing on canine gastric motility and emptying," Am J Physiol, vol. 265, pp. G767-G774, 1993.

Lin et al., "Effects of pacing parameters on entrainment of gastric slow waves in patients with gastroparesis," Am J Physiol, vol. 274, pp. G186-G191, 1998.

McCallum et al., "Gastric pacing improves emptying and symptoms in patients with gastroparesis," Gastroenterology, vol. 114, pp. 456-461, 1998.

Familoni et al., "Efficacy of electrical stimulation at frequencies higher than basal rate in canine stomach," Digestive Diseases and Sciences, vol. 42, No. 5, pp. 892-897, 1997.

Familoni et al., "Case Report: Electrical stimulation at a frequency higher than basal rate in human stomach," Digestive Diseases and Sciences, vol. 42, No. 5, pp. 885-891, 1997.

Xing et al., "The effect of gastric electrical stimulation on canine gastric slow waves," Am J Physiol Gastrointest Liver Physiol, vol. 284, pp. G956-G962, 2003.

Payne et al., "Bioelectric neuromodulation for gastrointestinal disorders: effectiveness and mechanisms," Nat Rev Gastroenterol Hepatol, vol. 16, No. 2, pp. 89-105, 2019.

Revicki et al., "Development and validation of a patient-assessed gastroparesis symptom severity measure: The Gastroparesis Cardinal Symptom Index," Aliment Pharmacol Ther, vol. 18, pp. 141-150, 2003.

Abell et al., "Gastric Electrical Stimulation in Intractable Symptomatic Gastroparesis," Digestion, vol. 66, pp. 204-212, 2002.

Gasser, "The Classification of Nerve Fibers," Ohio J Sci, vol. 41, pp. 145-159, 1941.

Cohen, "The statistical power of abnormal psychological research: a review," Journal of Abnormal Social Psychology, vol. 65, pp. 145-153, 1962.

Horn et al., "Delineation of vagal emetic pathways: Intragastric copper sulfate-induced emesis and viral tract tracing in musk shrews," Am J Physiol Regul Integr Comp Physiol, vol. 306, pp. R341-R351, 2014.

Wo et al. Gastric Electrical Stimulation for Gastroparesis and Chronic Unexplained Nausea and Vomiting. Curr Treat Options Gastro 14, 386-400, 2016.

* cited by examiner

SYSTEM AND METHOD FOR GASTRIC ELECTRICAL STIMULATION USING COMPOUND NERVE ACTION POTENTIAL FEEDBACK

CROSS-REFERENCE TO RELATED APPLICATIONS

The present patent application is related to and claims the priority benefit of U.S. Provisional Patent Application Ser. No. 62/979,351, filed Feb. 20, 2020, the contents of which are hereby incorporated by reference in its entirety into the present disclosure.

STATEMENT REGARDING GOVERNMENT FUNDING

This invention was made with government support under OD023847 and OD028183 awarded by the National Institutes of Health. The government has certain rights in the invention.

TECHNICAL FIELD

The present disclosure generally relates to implantable devices, and in particular, to a gastric electric stimulation system with vagal compound nerve action potential feedback for control of the system parameters.

BACKGROUND

This section introduces aspects that may help facilitate a better understanding of the disclosure. Accordingly, these statements are to be read in this light and are not to be understood as admissions about what is or is not prior art.

Gastroparesis (GP) is a chronic gastrointestinal disorder characterized by a delayed clearance of food from the stomach to the small intestine. The primary symptoms are nausea (about 92%), vomiting (about 84%), abdominal bloating (about 75%) and early satiety (about 60%). A diagnosis is based on gastric emptying scintigraphy and the presence of one or more characteristic symptoms of gastroparesis for more than 3 months.

Gastric electrical stimulation (GES) of the stomach, including presumably local vagal branches is an effective treatment for nausea and vomiting, although less effective in augmenting emptying, in gastroparesis patients who have been refractory to other forms of medical therapy. How GES relieves nausea and vomiting in symptomatic patients is unclear. Human studies of gastroparetic patients using positron emission tomography (PET) scanning show that GES produces changes in blood flow to specific areas of the central nervous system. Experiments in anesthetized rodents show that GES of the antrum and stimulation of the cervical vagus nerve produce vagal compound nerve action potentials (CNAPs) that can be measured with implanted cuff electrodes and with Ag/AgCl disk electrodes positioned on the skin surface over the mid cervical vagal nerves.

However, despite decades of research, the optimal GES parameters for treating the specific symptoms of gastroparesis remain unclear, as do the mechanisms behind their reported efficacy. There are two broad classes of stimulus parameters: High frequency/short-pulse stimuli, which are in clinical use, and low frequency/long-pulse stimuli, which are not in clinical use. Both are reported as effective for relieving symptoms of nausea and vomiting, but only the latter has been shown to entrain gastric electrical activity and promoting gastric motility.

In practice, physicians select a first set of GES parameters for a patient, wait a few weeks, then ascertain if the symptoms have improved. In response to the patient's answers (e.g., visual-analog scale (VAS) based symptom surveys, e.g., Gastroparesis Cardinal Symptom Index (GCSI) Survey, are used to keep track of changes in gastroparesis-related symptoms from GES), the physician makes changes to the GES parameters and repeats the same process. This open-loop approach takes a considerable amount of time and can be frustrating for both the patient and the physician.

Therefore, there is an unmet need for a novel approach to provide a patient-specific targeted solution for determining GES parameters.

SUMMARY

A gastric electric stimulation system is disclosed. The system includes a processing system having a processor. The system further includes at least one of a left vagus nerve sensor and a right vagus nerve sensor coupled to the processing system. The processing system is configured to receive a model which statistically correlates sensed compound nerve action potential (CNAP) parameters measured from at least one of left and right vagus nerves of subjects within a population to feedback surveys of the subjects in the population corresponding to a plurality of gastric symptoms and symptom parameters. The processing system is further configured to receive one or more gastric symptoms of a subject outside of the population ($Subject_{out}$), the processing system is configured to from the model determine CNAP parameters that correspond to the gastric symptoms with least severity ($CNAP_{min}$), measure CNAP activity of the Subjectout from the at least one of left and right vagus nerve sensors while modifying gastric electrical stimulation (GES) parameters for the Subjectout from a plurality of predetermined GES parameters, and select the GES parameters from the plurality of predetermined GES parameters that corresponds to the CNAPmin ($GES_{out}$). The processing system is then configured to output the $GES_{out}$.

A method of gastric electric stimulation is also disclosed. The method includes receiving at least one of a left vagus nerve sensor output and a right vagus nerve sensor output, the method also includes receiving a model which statistically correlates sensed compound nerve action potential (CNAP) parameters measured from at least one of left and right vagus nerves of subjects within a population to feedback surveys of the subjects in the population corresponding to a plurality of gastric symptoms and symptom parameters. Furthermore, the method includes receiving one or more gastric symptoms of a subject outside of the population ($Subject_{out}$), from the model determining CNAP parameters that correspond to the gastric symptoms with least severity ($CNAP_{min}$), measuring CNAP activity of the $Subject_{out}$ from the at least one of left and right vagus nerve sensors while modifying gastric electrical stimulation (GES) parameters for the $Subject_{out}$ from a plurality of predetermined GES parameters, and selecting the GES parameters from the plurality of predetermined GES parameters that corresponds to the $CNAP_{min}$ ($GES_{out}$). The method then includes outputting the $GES_{out}$.

BRIEF DESCRIPTION OF DRAWINGS

FIG. 1B shows a closer depiction of the electrode placement with respect to gastric branches of the vagus nerve that supply sensory and motor functions to the stomach.

FIG. 4F shows results for the 35 subjects with idiopathic gastroparesis, FIG. 4G shows results for the 19 subjects with type 2 diabetic gastroparesis, and FIG. 4H shows results for the 9 subjects with type 1 diabetic gastroparesis.

DETAILED DESCRIPTION

Figure 1A:
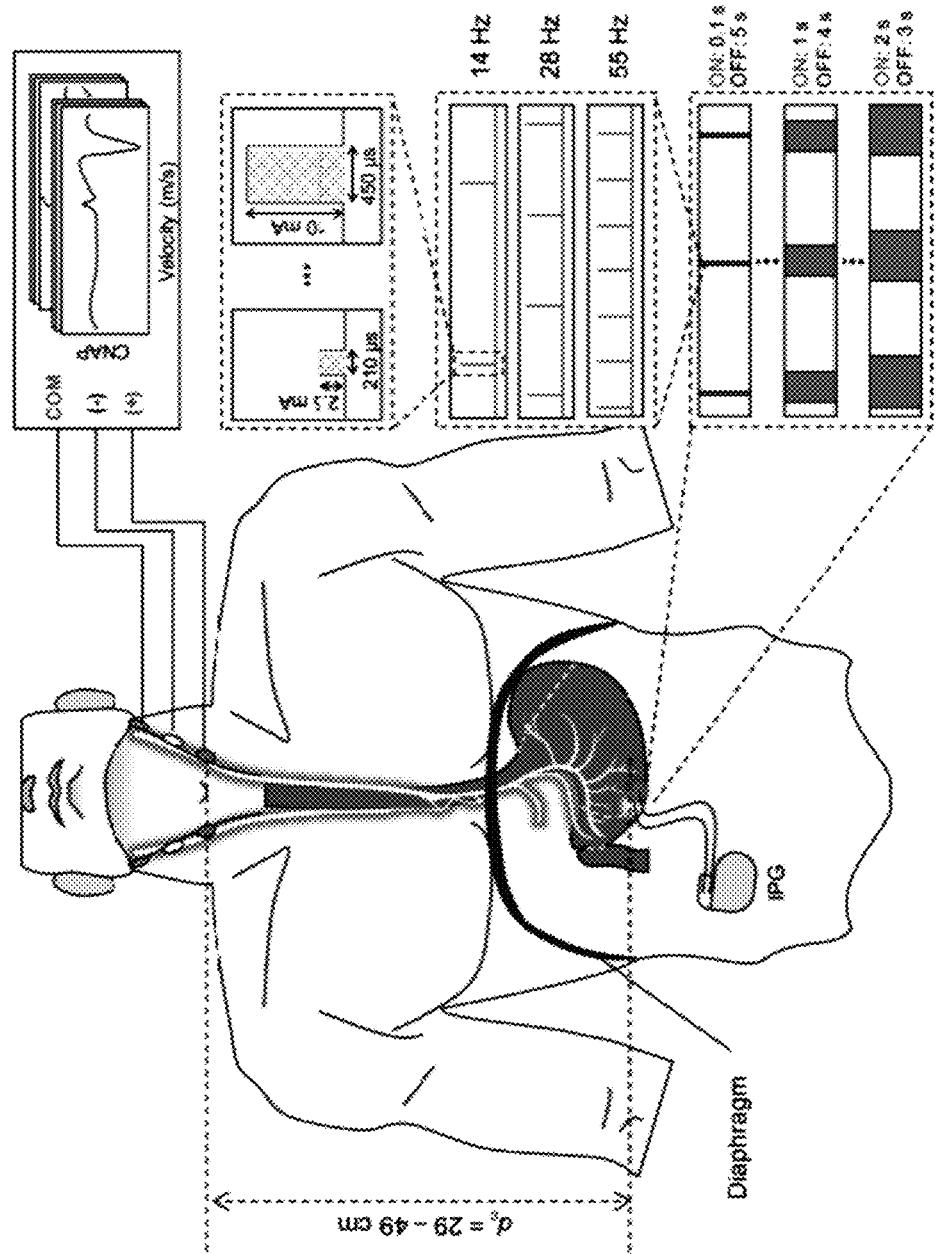
FIGS. 1A and 1B are schematics of a human subject with an implanted GES system with associated electrodes and vagal nerve recording sensors.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

A novel approach to provide a patient-specific targeted solution for determining gastric electrical stimulation (GES) parameters is presented. Towards this end, an approach based on vagal nerve recording is presented that can provide a compound nerve action potential (CNAP) feedback-based system utilized for patient-specific GES parameters.

Clinical GES parameter selections are not effective for promoting motility, and since the vagus is the primary nerve supply to the stomach, GES likely modulates nausea and vomiting through a vagal mechanism. Due to the natural variation in disease etiology and GES electrode placement relative to gastric vagal afferent fibers, along with inherent anatomical and physiological differences, each patient will likely require a unique, personalized set of stimulus parameters and electrode placements to engage specific vagal afferent pathways that mediate effective GES therapy.

Figure 1B:
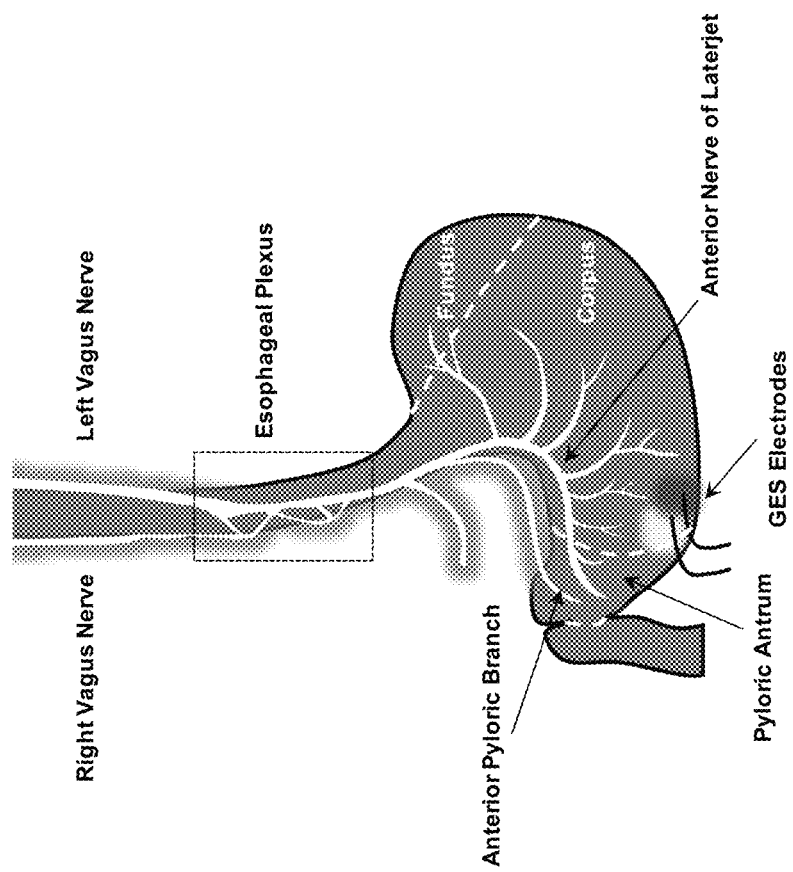

Patients who have an implanted GES device undergo intermittent stimulation of the stomach wall through bipolar wire electrodes implanted along the greater curvature of the ventral stomach approximately 10 cm proximal to the pylorus. Referring to FIGS. 1A and 1B, schematics of a human subject with an implanted GES system with associated electrodes and vagal nerve recording sensors is provided (FIG. 1B shows a closer depiction of the electrode placement with respect to gastral physiology). The GES electrodes are implanted 10 cm proximal to the pylorus along the greater curvature of the stomach. The bipolar stimulating electrodes are implanted approximately 1 cm apart with a slight bias toward the anterior (or ventral) wall of the stomach. FIG. 1B shows the approximate location of these implanted GES electrodes in relation to the anterior nerve of Laterjet, which arises from the anterior gastric branch of the anterior abdominal vagal trunk, and in relation to the pyloric branch(es) of the vagus nerve, which arise from the hepatic branch of the anterior abdominal vagal trunk to supply the pylorus.

Based on the location of the stimulating electrodes, the signals that were measured from the skin surface overlying the left cervical vagus nerve would most likely come from fibers contained within the branches that project from the anterior nerve of Laterjet near the junction of the corpus and pyloric antrum. The source of the signals observed overlying the right cervical vagus nerve is less certain, since the electrodes are implanted on the ventral wall of the stomach, which are expected would only produce action potentials that could be observed along the left vagus nerve. It can thus be speculated that the right vagal signal is due to 1) direct activation of dorsal gastric fibers resulting from the large stimulus currents employed in GES (unlikely), 2) crosstalk between the left and right vagus nerve via communicating branches that are believed (but to our knowledge not proven in human subjects) to exist within the esophageal plexus, or 3) as a result of vagal reflexes initiated by left vagal afferent activation (which could perhaps result in an efferent signal from the right vagus nerve).

Electrodes are always implanted in this manner and are always separated by 1 cm. The stimulus is delivered through the stimulating leads by an implantable pulse generator (IPG) that is placed subcutaneously in the abdominal region. These impulses are typically delivered with a stimulus pulse. The stimulus pulse has a current range of between about 1 mA to about 10 mA, and according to one embodiment the stimulus pulse has a current of 2.5 mA, 5 mA, 7.5 mA, or 10 mA. The stimulus pulse has a pulse duration of between about 200 µs to about 500 µs, and according to one embodiment the stimulus pulse has a pulse duration of 210 µs, 330 µs, or 450 µs. The stimulus pulse has frequency range of about 10 Hz to about 60 Hz, and according to one embodiment the stimulus pulse has a frequency of 14, 28, or 55 Hz. According to one embodiment, the stimulus pulse has a repetition frequency of about 0.1-2 s ON time, and a 3-5 s OFF time. The amplitude, frequency and pulse duration of these stimuli are typically varied over time according to a protocol provided by the GES manufacturer to methodically identify a combination of parameters that patients report as beneficial. These settings can be changed with an external wand that is placed on the patient's abdomen overlying the IPG. As discussed in the background section of the present disclosure, since no physiological feedback signals are measured, the process of methodically changing the parameters can take months to complete and is not specific to a patient's symptoms. Referring back to FIG. 1A, the panels show example parameters, as discussed above. FIG. 1A also shows vagal recording sensor positioned on the neck (both right and left sensors are shown). Also shown is a parameter referring to the distance between the GES electrodes and the vagal sensors, referred to as the $d_c$. Conduction velocity (i.e., speed) of nerve transmission can be computed by dividing the conduction distance, $d_c$ (measured from the center of skin surface over the deduced stimulating electrode location to the distal recording electrode, in mm), by the latency, $t_c$ (in ms), of each sample relative to the start of a stimulus pulse. These parameters are further discussed below.

Figure 1C:
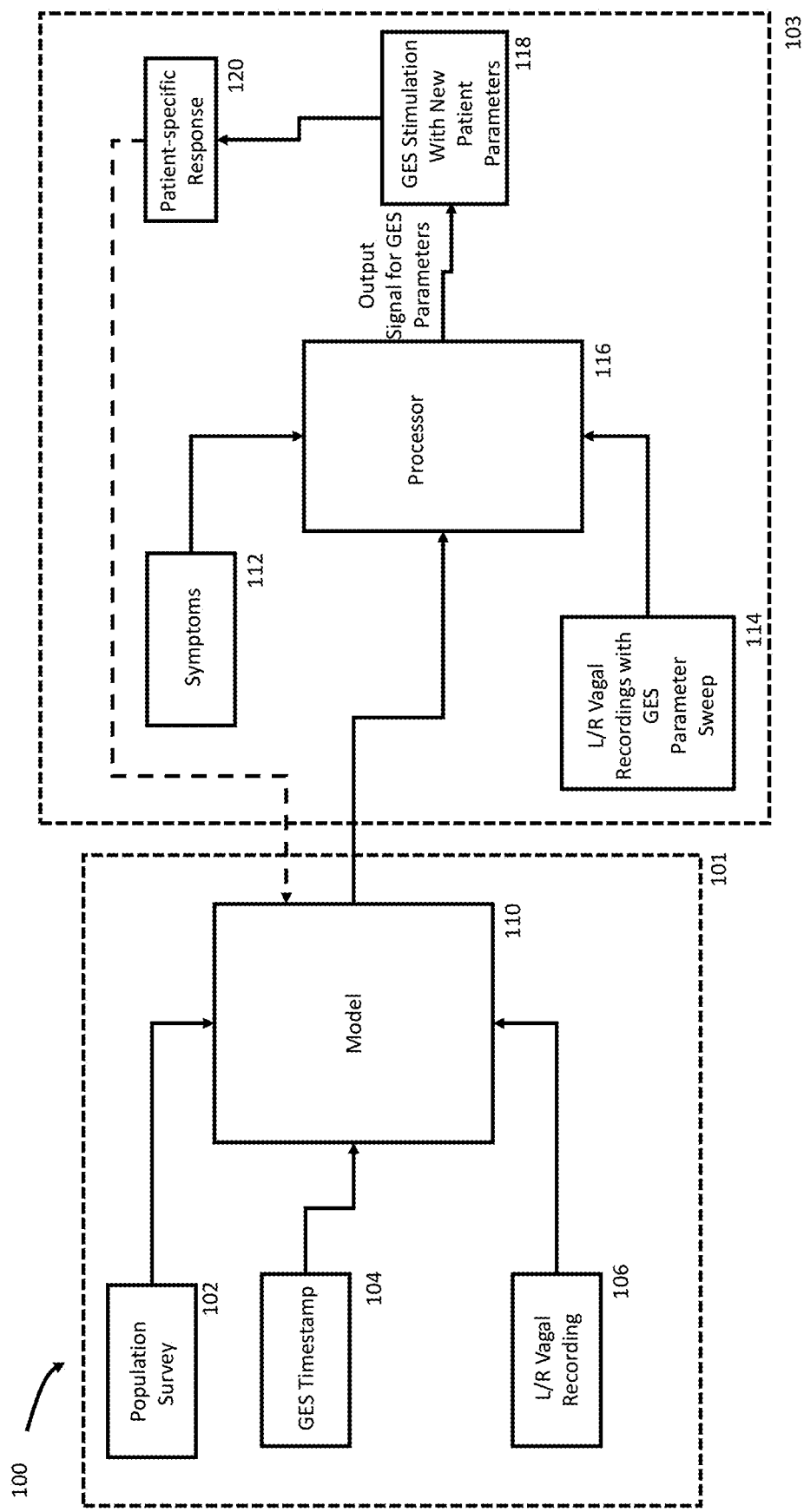
FIG. 1C is a high-level diagram for the gastric electrical stimulation system of the present disclosure.

With this general background, reference is now made to FIG. 1C which is a high-level diagram for the GES system 100 of the present disclosure. The GES system 100 of the present disclosure, is based on two major subsystems: the modeling subsystem 101 and the processing subsystem 103. The modeling subsystem 101 includes several blocks: population survey block 102, GES timestamp block 104, and at least one of left and right (L/R) vagal recording block 106 all feeding a central modeling block 110. The survey block 102, further discussed below, provides results of surveys from a plurality of subjects that are members of a population of subjects. The surveys include responses from the subjects associates with symptoms which include nausea, vomiting, early satiety, bloating, fullness, epigastric pain, epigastric burn, cardiac pain, and cardiac burn. The surveys may optionally also include underlying diseases borne by the subjects. The diseases may include type-I diabetes, type-II diabetes, post-surgical gastroparesis, and post-viral/bacterial gastroparesis. Additionally, the surveys may optionally include other parameters such as gender, race, and body mass. The central modeling block 110 further receives input from the GES timestamp block 104. The GES timestamp block 104 provides timestamps of GES stimulus onset for each stimulus pulse. As discussed below, electrocardiogram (EKG) can be used to establish the timestamp. This GES timestamp block 104 is active during a subject's visit during which not only the GES stimulation takes place according to a prescribed set of parameters (these parameters may vary from subject-to-subject), while obtaining vagal recording 106 from at least one of left and right vagus nerves, obtained from the L/R vagal recording block 106. Therefore, each timestamp in GES timestamp block 104 is associated with a corresponding L/R vagal recording in block 106. These inputs to the central modeling block 106, as discussed in detail below, are used to provide a statistical model which statistically correlates CNAP parameters measured from the at least one of left and right vagus nerves of the subjects within the population to the feedback surveys of the subjects in the population corresponding to a plurality of gastric symptoms and symptom parameters. The symptom parameters of the plurality of gastric symptoms include severity, frequency, and duration. Severity may include a scale of 0, 1, 2, 3, or 4, wherein 0 refers to no symptom, and 4 refers to a highest severity for an associated symptom of the plurality of gastric symptoms. CNAP parameters may include Aβ, Aγ, and Aδ, B, and C, as known to a person having ordinary skill in the art.

The central modeling block 110, then provides a statistical correlation between subject symptoms and CNAP parameters. This correlation can then be used to search for an effective set of GES parameters for a patient-specific treatment protocol in the form of a feedback methodology. This feedback methodology is shown with respect to the processing subsystem 103.

The processing subsystem 103 includes a processor with several inputs from associated blocks: a symptom block 112 which provides symptoms of a patient that was not part of the original population used to build the model (this patient is referred to herein, inter alia, as $Subject_{out}$), the central modeling block 110, and L/R vagal recording block 114 which provides at least one of the left and right vagal recordings associated with a sweep of GES parameters. Thus, when a new patient enters a physician's office, first the patients symptoms, see above, is ascertained (block 112) and provided to the processor 116. Next the GES parameters are swept according to a matrix. According to one embodiment, 12 entries (e.g., 4 current amplitudes, see above, and 3 pulse widths, see above) are used to generate the matrix. The entries of the matrix are sequenced one-by-one, all while L/R vagal recordings are recorded and provided to the processor 116. The processor 116 using the central modeling block's input, determines the optimum CNAP parameters (identified herein, inter alia, $CNAP_{min}$) that best reduce the symptoms from the symptom block 112. This optimum match is then compared against the recorded L/R vagal recordings provided by the block 114. Once a match or a close match is identified against the L/R vagal recordings, the processor 116 provides an output signal representing the best selection for the GES parameters (identified hereinafter, inter alia, $GES_{out}$). This output is provided to the GES stimulator, as provided in block 118. With that, after a predetermined amount of time, the $Subject_{out}$ response, shown in block 120, is optionally provided back to the central modeling block 110. The response includes patient-related parameters, wherein the patient-related parameters include diseases, gender, race, and body mass index. The diseases as discussed above include type-I diabetes, type-II diabetes, post-surgical gastroparesis, and post-viral/bacterial gastroparesis.

The present disclosure provides a system and method to noninvasively resolve important features of the GES-evoked vagal CNAP responses in human subjects, using validated gastroparesis symptom survey data and traditional approaches to CNAP analysis to resolve associations between phase-locked CNAP responses to GES and patient symptom profiles. Using this tool for GES from the skin surface, the present disclosure provides data which shows that the GES-mediated recruitment of specific vagal nerve fiber populations, grouped by their conduction speed, predict symptom improvement. This new approach to measure and classify vagal responses with respect to symptom profiles provides: 1) a method to measure vagal nerve activation in a completely noninvasive manner, and confirm observed clinical outcomes; 2) a data-driven path to develop a diagnostic test that determines if and how a patient might benefit from GES therapy; 3) a data-driven approach to better manage symptoms in existing patients receiving GES therapy using the vagal response as feedback to titrate GES parameters; 4) a data-driven approach to identify nerve response patterns that predict off-target effects from stimulation; and 5) a new set of tools to help others inform the design and functionality of bioelectronic interventions for gastroparesis and other indications.

To build the model (see the central modeling block 110 in FIG. 1C), a study was carried out, as discussed. Sixty six subjects were included as part of the study. As a pure observational study, the design for the central modeling block 110 did not alter patient treatment in any way (i.e., the device was not reprogrammed from the prescribed settings, there were no change any medication use, no changes in their diet, and no expectation were provided that the study or its outcome would provide any potential benefit to the patient). This observational study approach provided a unique neural response marker discovery platform through which study data could be screened for any potential associations between evoked responses measured from the electrodes placed on the skin surface over the left/right cervical vagus nerve and symptom profiles collected through a visual analog scale at the time of data collection. Importantly, the observational study design was expected to reduce or eliminate any possibility of a placebo effect, because patient treatment plans were not altered in any way.

Subjects were asked to complete the Gastroparesis Cardinal Symptom Index (GCSI) symptom survey, a gold standard known to a person having ordinary skill in the art, after providing informed consent to enroll into the study. The data collection expert, who was responsible for collecting all study data and maintaining confidentiality, interrogated the GES device of each subject prior to placing the cervical recording electrodes. This was done in order to identify and document the existing/prescribed stimulus parameters, the impedance between the stimulating electrodes, and the output voltage setting of the device (the specific GES device used sets the stimulus current by applying a voltage computed according to the measured resistance of the electrodes via Ohm's law). After instructing the subject to lay down on their back, the skin surface overlying the left and right cervical vagus nerve was cleaned with alcohol swabs and allowed to dry.

A pair of cutaneous recording electrodes (conventional Ag/AgCl gel pad electrodes that are used to collect electrocardiogram data) were placed on the skin surface of the neck overlying the left and/or right mid-cervical vagus nerve (see FIG. 1A), spaced about 3 cm apart within the carotid triangle, with the active electrode just medial to the border of the sternocleidomastoid and lateral to the laryngeal prominence, and the reference electrode about 3 cm superior to the active electrode along the medial border of the ipsilateral sternocleidomastoid (the area described is located slightly anterior to the sternocleidomastoid muscle, just inferior to the angle of the jaw and superior to its clavicular insertion). A large surface area common ground/reference electrode was placed on the xiphoid process or ipsilateral mastoid. To facilitate the recording process, a pea-sized drop of conductive electrolyte gel was applied to the center of each EKG electrode before placing it on the skin. After connecting the electrodes and prior to data acquisition, the distance that a nerve signal would be expected to travel before reaching the first recording electrode was estimated by measuring the distance between the surface position deduced to overlie the implanted GES electrodes and the distal left cervical recording electrode (i.e., the first cutaneous electrode that an afferent vagal signal would pass on its way from the stomach to the solitary nucleus). This critical measurement was necessary to standardize the classification of CNAP data collected from different subjects with different vagal nerve lengths (i.e., different patient heights). The conduction distance was always measured by the same investigator following the same procedure.

All data were collected with the ADINSTRUMENTS POWERLAB data acquisition system via their OCTALBIOAMP analog front end or their electro-oculogram (EOG) pods. A Lead I electrocardiogram (EKG) was measured during acquisition, which was later conditioned and used to detect the GES-generated stimulus artefacts (and thus the timing of GES stimulation, i.e., GES timestamps). Recordings were collected for 3-5 min at the patient's prescribed GES parameters, followed by 3-5 min of recording with the device off, and finally by 3-5 min of recording with the device turned back on again. All data were digitized at 10 kHz and de-identified prior to handing the raw recordings and conduction distance for further processing and analysis.

Clinical study data were analyzed in single-blind fashion using custom analysis scripts written in MATLAB R2015a. Analysis was performed on de-identified subject data with no prior knowledge of device settings, implant date, efficacy, or any other information beyond the location of the pad electrodes used to measure the data in Channels 1-3 of the ADINSTRUMENTS POWERLAB SYSTEM and the conduction distance (Ch1: EKG; Ch2: Left cutaneous vagal electroneurogram (ENG); Ch3: Right cutaneous vagal ENG). Care was taken to standardize the method of analysis and data interpretation for each subject. Ensemble averaging was one method used to standardize the analysis.

Figure 2A:
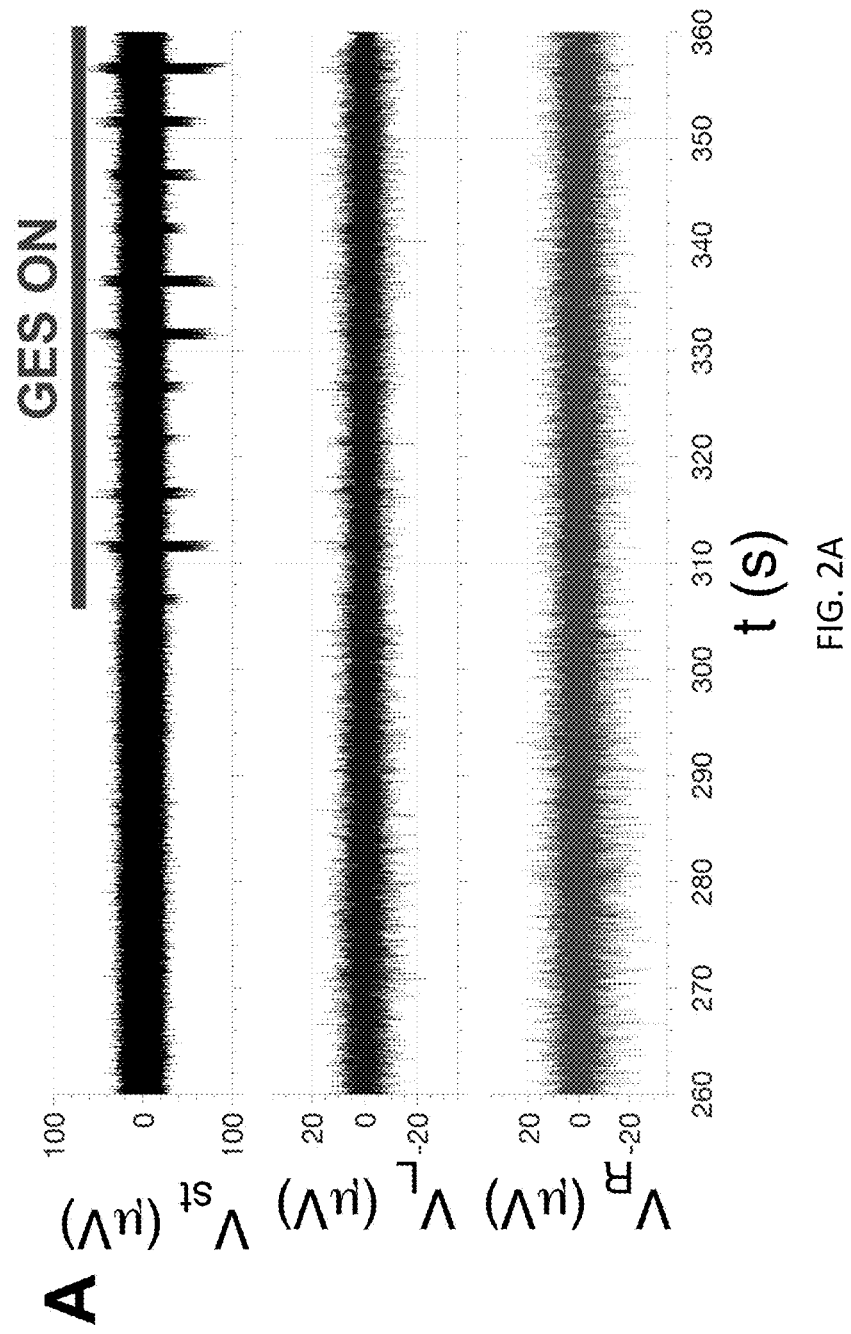
FIG. 2A is a complex graph plotting a right vagal sensor output, a left vagal sensor output, and a high-pass filtered EKG trace all vs. time in seconds, spanning between 260 and 360 seconds.
Figure 2B:
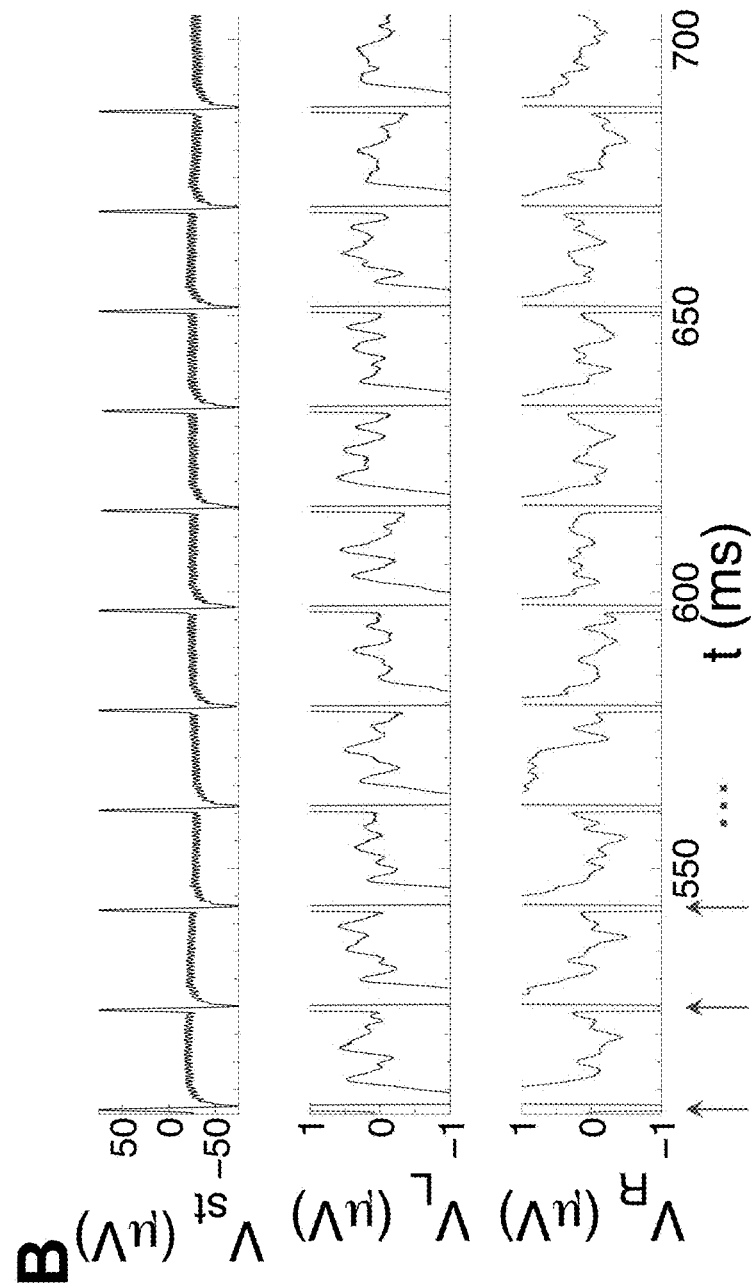
FIG. 2B is a small portion of the data provided in FIG. 2A, namely between 500 ms and 700 ms, which is a presentative data collected from one subject whose GES device was on and tuned to a pulse repetition frequency of 55 Hz, showing raw response data associated with GES visible in the left vagal and right vagal channels during the 18 ms intervals between stimulus artefacts.
Figure 2C:
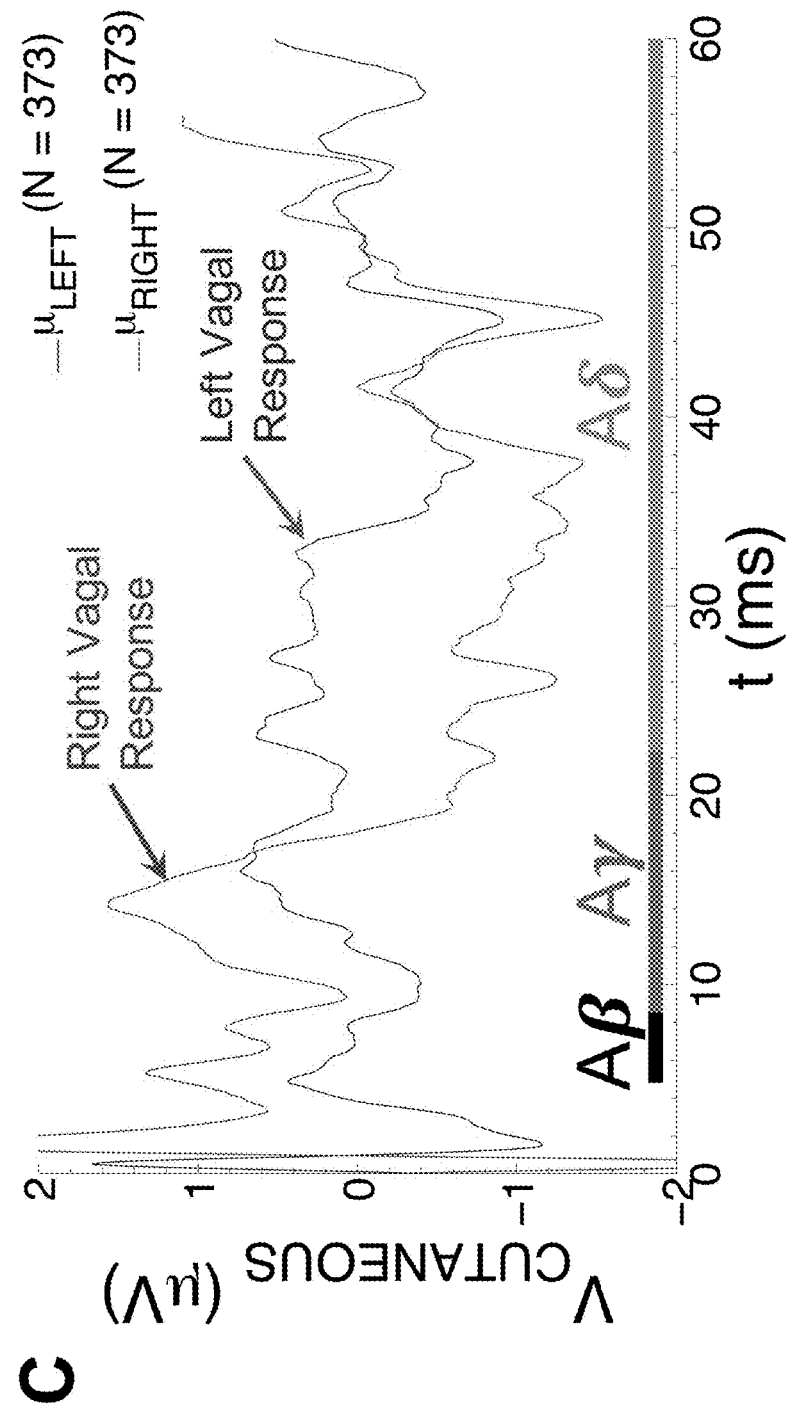
FIG. 2C is a plot of left and right vagal sensor output showing mean cutaneous responses recorded over the left and right vagus nerves of another subject whose GES device was on and tuned to a pulse repetition frequency of 14 Hz (mean of 373 responses).
Figure 2D:
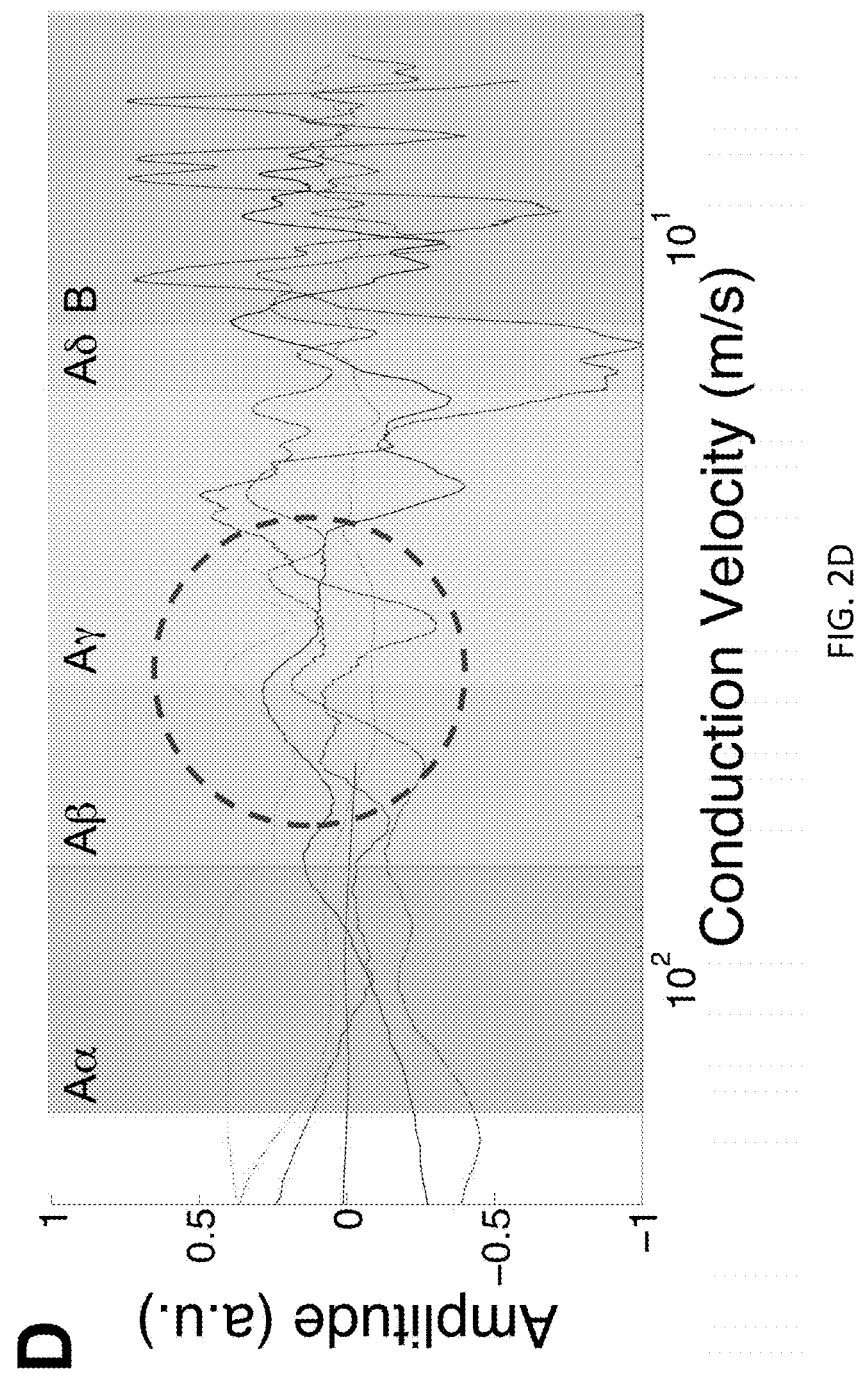
FIG. 2D is a plot of amplitude vs. conduction velocity in (m/s) showing output of classification of the A$\alpha$, A$\beta$, A$\gamma$ and A$\delta$ fibers based on conduction velocity.

A stimulus artefact template for ensemble averaging was formed from the mean of six randomly selected segments of data in the high pass-filtered EKG channel. In each case, the template started just prior to a stimulus artefact and ended just prior to the next stimulus artefact. According to one embodiment for a frequency setting of 14 Hz, the artefact template can be no longer in duration than approximately 71 ms. Referring to FIG. 2A, an example of the typical morphology of the stimulus artefact, in this case for a 55 Hz stimulus frequency having a period of approximately 18 ms, is shown. FIG. 2A is a complex graph plotting the right vagal sensor output, the left vagal sensor output, and the high-pass filtered EKG trace all vs. time in seconds, spanning between 260 and 360 seconds. FIG. 2B is a small portion of the data provided in FIG. 2A, namely between 500 ms and 700 ms, which is a presentative data collected from one subject (subject v003) whose GES device was on and tuned to a pulse repetition frequency of 55 Hz, showing raw response data associated with GES visible in the left vagal and right vagal channels during the 18 ms intervals between stimulus artefacts. Referring to FIG. 2C, mean cutaneous responses are shown recorded over the left and right vagus nerves of another subject (subject v011) whose GES device was on and tuned to a pulse repetition frequency of 14 Hz (mean of 373 responses). The time intervals where one would expect to find Aβ, Aγ and Aδ fiber responses are shown in the plot (time intervals were computed using the 33 cm conduction distance for subject v011). Referring to FIG. 2D, amplitude vs. conduction velocity in (m/s) is shown showing output of classification of the Aα, Aβ, Aγ and Aδ fibers based on conduction velocity. Mean left vagal cutaneous response to gastric electrical stimulation as a function of conduction velocity (i.e., speed) for six human subjects (normalized to the maximum response voltage detected among all six traces to aid visual comparison). Note that one trace only extends into the Aβ range and one trace only extends into the Aγ range. These traces are from subjects whose prescribed stimulus pulse repetition frequency was tuned to 55 Hz and 28 Hz, respectively, as opposed to the typical value of 14 Hz. The dashed oval is intended to highlight the relative consistency of the left vagal Aγ volley observed in different subjects.

Custom event detection workflow in MATLAB were devised to locate, extract, align and average all segments of the measured data that match the shape and timing of the stimulus artefact template (where the stimulus artefacts have a sufficient presence for software-based detection, almost always only in the EKG trace). The location of each stimulus artefact was first detected in the EKG trace via the normalized cross-correlation (NORMXCORR2 function in MATLAB) of the stimulus artefact template and a zero-phase, high pass-filtered replica of the EKG trace (fc=30 Hz; fp=50 Hz; a zero-phase, finite impulse response equiripple filter, designed to suppress the EKG signal, while preserving the shape and phase of the stimulus artefact with respect to the left and right cutaneous vagal recordings), i.e., GES timestamp. The output of the normalized cross-correlation function was cubed to further distinguish the regions where the template and portions of the EKG signal matched versus regions where they did not match (the rate of attenuation increases faster for smaller values closer to 0 than the larger values closer to 1 when multiplied by themselves). The cubed cross-correlation function (CCF) output was then fed into a function that detected the temporal position of peaks in the CCF output signal whose amplitude was greater than 0.9 (or 90% of the maximum possible signal amplitude). Next these time indices (i.e., the location of the start of each detected stimulus artefact in the file) were used to extract and average phase-locked response data from the left and right cutaneous vagal ENG recording channels. The number of stimulus-response segments extracted from each file depended on the recording duration and pulse repetition frequency setting on the device of each patient.

The mean stimulus-response waveforms, computed from an average of hundreds of GES-evoked responses extracted from the left and right cutaneous recording traces (up to 600+ in cases of 28 or 55 Hz stimulation), were then plotted as a function of conduction velocity (i.e., conduction speed) to account for differences in conduction distance among the pool of patient data (a method to standardize the data for population-based analysis by reducing the influence of CNAP conduction time differences between subjects that could result simply from a difference in the distance that the evoked signal had to travel before passing the first recording electrode, i.e., different heights). Conduction velocity (i.e., speed) was computed by dividing the conduction distance, $d_c$, see FIG. 1A (measured from the center of skin surface over the deduced stimulating electrode location to the distal recording electrode, in mm), by the latency, $t_c$ (in ms), of each sample relative to the start of a stimulus pulse. All subsequent analysis was performed in the conduction velocity domain in order to account for signal dispersion in the time domain that would prohibit the reliable identification of common features across subjects. The mean CNAP signal was then baseline-adjusted by subtracting the mean of all CNAP response samples from each CNAP response sample, which centered the signal around the 0 V line. The 95% confidence interval (1.96 times the standard error of the mean) about the mean CNAP response at successive sample was then computed in a similar manner (e.g., using each baseline-adjusted CNAP response detected from a subject) prior to the response classification step. For normally distributed data, the 95% confidence interval about the mean encloses any value within ±1.96* standard error of mean (s.e.m.)—which is computed by dividing the standard deviation by the square root of the sample size—1: i.e., s.e.m.=std./sqrt(n-1) of the mean value.

The baseline-adjusted, mean stimulus-response data (i.e., candidate CNAP) from the left and right vagal channels were next parsed by conduction velocity using the Letter System for nerve fiber classification, known to a person having ordinary skill in the art. Within the confines of the Letter System, mean CNAP response volleys from each subject were then classified in terms of I) showing a significant response (e.g., presence of an Aβ/Aγ response whose magnitude is significantly different from 0 V at α=0.05), II) not showing a response (e.g., no fiber response volleys are detected and/or the magnitude of the response volley is not significantly different from 0 V at α=0.05), or III) data are corrupted by noise, identified as high-amplitude, highly-periodic oscillations that match 60 Hz line noise or any of its harmonics. The output of this analysis was a set of eight binary outcomes for each subject: 0 for each insignificant fiber response and 1 for each significant fiber response, defined as having an amplitude in a particular conduction band of the Letter System whose amplitude is significantly different from 0 V at α=0.05. More specifically, these 8-digit codes represented the "nerve response signatures" from the left and right vagus nerve of each subject as a set of numbers that indicate a detectable response (1) or no detectable response (0) from left vagal Aβ, Aγ and Aδ, B fibers and right vagal Aβ, Aγ and Aδ, B fibers. Since the Aδ fiber conduction velocity range from our classification system (CV: 5-15 m/s) overlaps with the B fiber conduction velocity range (CV: 3-14 m/s), the B fiber classification was limited to only survey the signal from 3-5 m/s. The stimulus pulse frequency and long conduction distances (between about 29 and about 49 cm, see FIG. 1A) prevented us from assessing the response data for any form of C fiber activity as per the measurement protocol described above. If the circumstances of recording prevented us from resolving B fiber (or other) data, the corresponding position in the 8-digit code was left blank to avoid influencing the symptom parity analysis. It is important to note that these conduction velocity estimates could be overestimating or underestimating the true values, because the length of the nerve could not be measured or the precise point of vagal activation. Care must therefore be taken to have one investigator consistently perform these measurements in the same manner. This approach ensures that the data can be treated equally within the confines of this protocol.

After the mean cutaneous vagal responses were processed and classified as described above, the GCSI symptom survey data, GES parameter settings, age, gender and disease etiology data were made available in order to identify whether features of the cutaneous vagal recordings predict differences in gastroparesis symptoms. All statistical analysis was performed with STATA 14.2. Using STATA 14.2, symptom scores were compared between groups of subjects with significant [CNAP(+)] or without significant [CNAP(−)] left or right vagal Aβ, Aγ and Aδ, B fiber responses, defined as volleys in the mean response to GES whose peak amplitude is significantly different from 0 V at $\alpha=0.05$. More specifically, the difference in the mean symptom scores was determined as reported by patients with a particular type of nerve response and those without that same response was significantly different from 0 (at $\alpha<0.05$).

The unpaired t-test with Welch approximation, known to a person having ordinary skill in the art, was used for all symptom parity comparisons, assuming unequal variances within the symptom data belonging to each subgroup. For all comparisons, data were reported as a difference in mean symptom scores among a subgroup with and without a particular fiber response to GES (mean±s.e.m.). A negative number indicated that the subgroup with the particular fiber response shown on the x-axis labels reported, on average, a less severe and/or frequent incidence of that symptom than those without the same fiber response profile.

Referring back to FIG. 2B, as discussed above, an example cutaneous response data is provided measured from a single patient while the stimulator was on and tuned to a stimulus pulse repetition frequency of 55 Hz, which made it easy to observe raw responses to a train of stimuli (including stimulus artefacts detected from the high pass-filtered EKG trace, cutaneous recording over the left vagus nerve, and cutaneous recording over the right vagus nerve). Arrows in FIG. 2B show the locations of the stimulus artefacts, which were detected offline from the filtered EKG trace with custom software and used to extract the segments of data following each stimulus. The cutaneous response to each stimulus was then averaged to boost the signal-to-noise ratio of the evoked response measured from the skin surface over the left and right cervical vagus nerve.

As alluded to above, FIG. 2D overlays the mean left vagal cutaneous response to gastric electrical stimulation as a function of conduction velocity for six subjects. The amplitude of each trace was normalized to the maximum amplitude within each trace to further highlight common features among responses from different subjects. The shaded regions denote the conduction velocity range associated with Aα (70-120 m/s), Aβ (40-70 m/s), Aγ (15-40 m/s), Aδ (5-15 m/s) and B (3-14 m/s) fibers in the Letter System (the C fiber conduction velocity range is not shown since its expected latency, on average, exceeds the latency between stimulus pulses delivered by the GES device). Note the prominence and consistency of the response peaks that fall within the Aβ/Aγ range (as emphasized with the dashed circle).

Figure 3A:
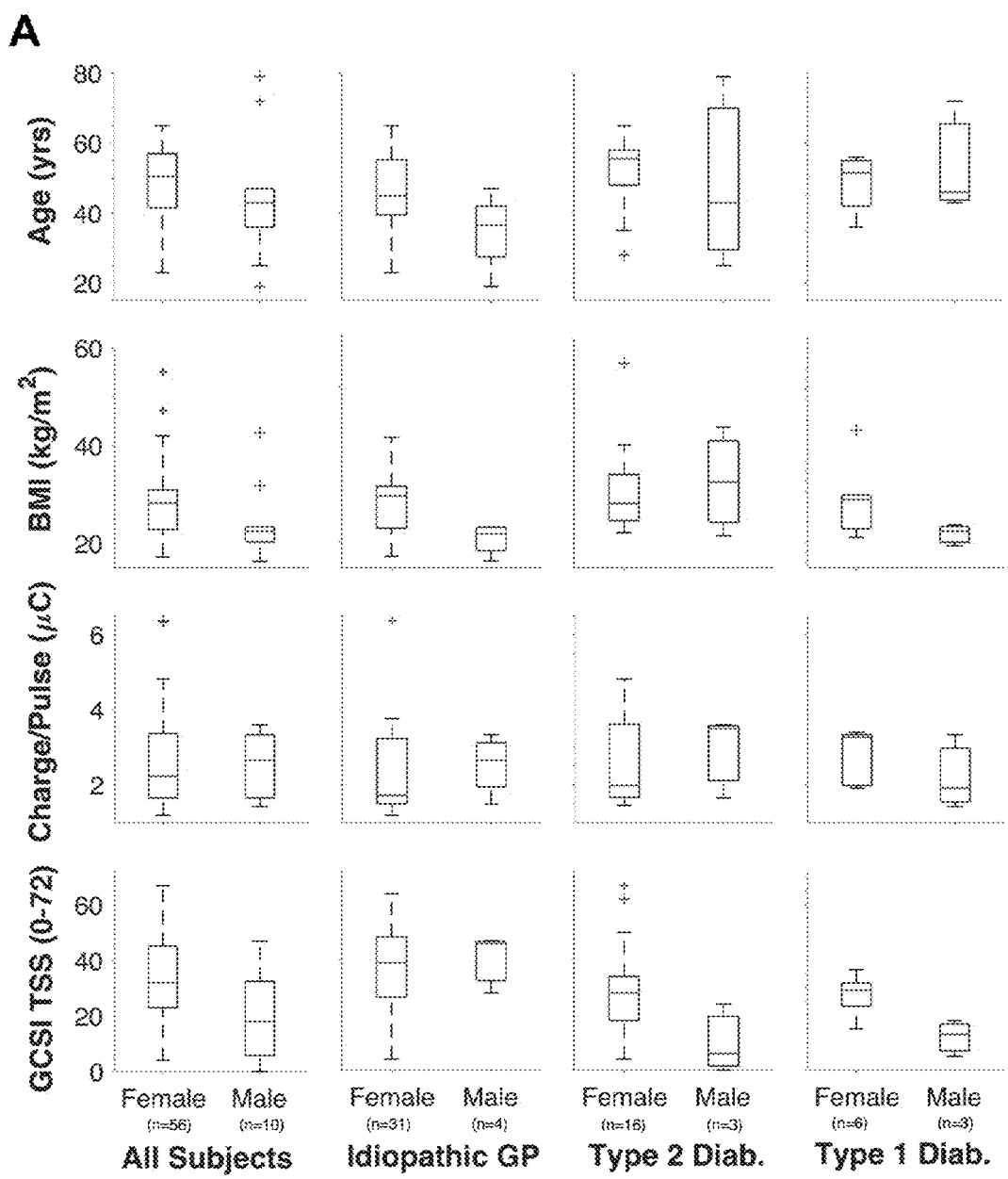
FIG. 3A is a complex plot presenting a summary of subject age, body mass index (BMI; in kg/m$^2$), stimulus strength (in $\mu$C per pulse), and total symptom score (TSS) for all subjects, subjects with idiopathic gastroparesis, subjects with type 2 diabetic gastroparesis, and subjects with type 1 diabetic gastroparesis.
Figure 3B:
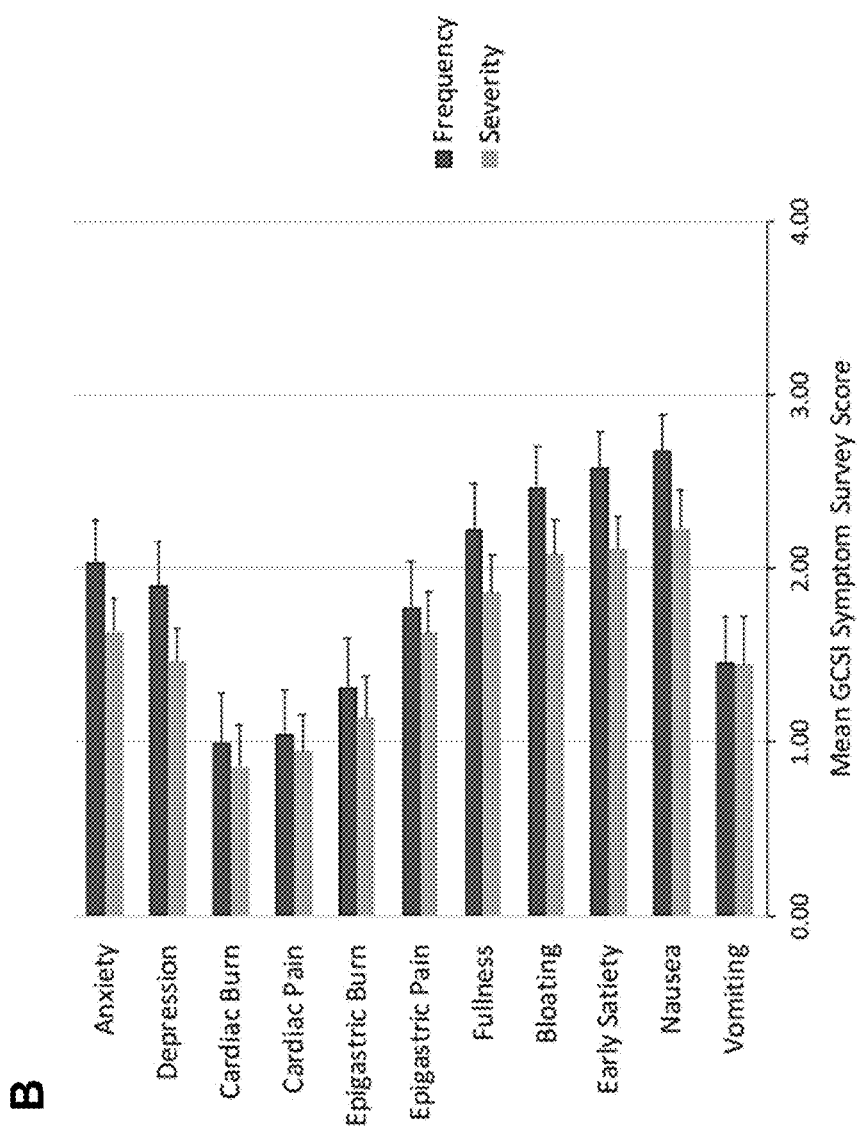
FIG. 3B is a graphical summary of symptom survey results from all 66 subjects included in this analysis.

Of the 66 subjects included in this analysis, 28 had diabetic GP (type 1:9; type 2:19), 35 had idiopathic GP, and 3 had postsurgical GP. Mean stimulus parameter settings do not significantly differ according to gender or disease etiology (mean stimulus pulse current=7.7±3.46 mA). GCSI symptom survey data are summarized in Table 1 by gender and disease etiology and graphically for the entire study population in FIGS. 3A and 3B. FIG. 3A is a complex plot presenting a summary of subject age, BMI (in kg/m$^2$), stimulus strength (in μC per pulse), and total symptom score (TSS) for all subjects (column 1), subjects with idiopathic gastroparesis (column 2), subjects with type 2 diabetic gastroparesis (column 3), and subjects with type 1 diabetic gastroparesis (column 4). FIG. 3B is a graphical summary of symptom survey results from all 66 subjects included in this analysis.

Table 1 presents the GCSI survey response summary

TABLE 1

Gastroparesis Cardinal Symptom Index (GCSI) survey response summary*

| GCSI Symptom | Descriptors | Sex | Type 1 Diab. | Type 2 Diab. | Idiopathic | Postsurgical | Combined |
|---|---|---|---|---|---|---|---|
| Nausea | Frequency | M | 1.67 ± 1.15 | 1.33 ± 1.15 | 3.25 ± 0.96 | — | 2.20 ± 1.32 |
| | | F | 1.83 ± 1.17 | 2.67 ± 1.40 | 3.00 ± 1.31 | 3.00 ± 1.00 | 2.77 ± 1.32 |
| | | M + F | 1.78 ± 1.09 | 2.44 ± 1.42 | 3.03 ± 1.26 | 3.00 ± 1.00 | 2.68 ± 1.33 |
| | Severity | M | 2.67 ± 1.53 | 1.33 ± 1.15 | 2.75 ± 0.50 | — | 2.30 ± 1.16 |
| | | F | 1.50 ± 0.84 | 2.13 ± 1.36 | 2.47 ± 1.09 | 1.67 ± 1.15 | 2.22 ± 1.17 |
| | | M + F | 1.89 ± 1.17 | 2.00 ± 1.33 | 2.50 ± 1.04 | 1.67 ± 1.15 | 2.23 ± 1.16 |
| Vomitting | Frequency | M | 1.33 ± 1.53 | 0.33 ± 0.58 | 2.25 ± 0.96 | — | 1.40 ± 1.26 |
| | | F | 0.80 ± 0.84 | 1.29 ± 1.33 | 1.72 ± 1.35 | 1.00 ± 1.00 | 1.47 ± 1.30 |
| | | M + F | 1.00 ± 1.07 | 1.12 ± 1.27 | 1.78 ± 1.31 | 1.00 ± 1.00 | 1.46 ± 1.28 |
| | Severity | M | 1.67 ± 2.08 | 1.33 ± 2.31 | 2.00 ± 1.15 | — | 1.70 ± 1.64 |
| | | F | 0.50 ± 0.55 | 1.50 ± 1.55 | 1.56 ± 1.19 | 1.00 ± 1.00 | 1.40 ± 1.27 |
| | | M + F | 0.89 ± 1.27 | 1.47 ± 1.61 | 1.61 ± 1.18 | 1.00 ± 1.00 | 1.45 ± 1.32 |
| Early Satiety | Frequency | M | 0.67 ± 1.15 | 0.00 ± 0.00 | 3.00 ± 1.15 | — | 1.40 ± 1.65 |
| | | F | 2.50 ± 1.05 | 1.80 ± 1.15 | 2.87 ± 1.28 | 2.67 ± 1.53 | 2.80 ± 1.21 |
| | | M + F | 1.89 ± 1.36 | 2.33 ± 1.50 | 2.89 ± 1.25 | 2.67 ± 1.53 | 2.58 ± 1.37 |
| | Severity | M | 0.33 ± 0.58 | 0.00 ± 0.00 | 2.75 ± 0.50 | — | 1.20 ± 1.40 |
| | | F | 2.17 ± 0.75 | 2.06 ± 1.24 | 2.39 ± 1.20 | 2.33 ± 1.15 | 2.27 ± 1.15 |
| | | M + F | 1.56 ± 1.13 | 1.74 ± 1.37 | 2.43 ± 1.14 | 2.33 ± 1.15 | 2.11 ± 1.24 |
| Bloating | Frequency | M | 0.67 ± 1.15 | 0.67 ± 1.15 | 2.50 ± 1.29 | — | 1.40 ± 1.43 |
| | | F | 2.25 ± 1.54 | 2.73 ± 1.10 | 2.65 ± 1.35 | 3.33 ± 0.58 | 2.67 ± 1.26 |
| | | M + F | 1.72 ± 1.56 | 2.39 ± 1.33 | 2.63 ± 1.32 | 3.33 ± 0.58 | 2.47 ± 1.36 |
| | Severity | M | 0.67 ± 1.15 | 0.67 ± 1.15 | 1.50 ± 0.58 | — | 1.00 ± 0.94 |
| | | F | 2.00 ± 1.41 | 2.25 ± 1.18 | 2.26 ± 1.18 | 3.00 ± 0.00 | 2.27 ± 1.17 |
| | | M + F | 1.56 ± 1.42 | 2.00 ± 1.29 | 2.17 ± 1.15 | 3.00 ± 0.00 | 2.08 ± 1.22 |
| Fullness | Frequency | M | 0.67 ± 1.15 | 0.33 ± 0.58 | 3.00 ± 1.00 | — | 1.33 ± 1.50 |
| | | F | 2.17 ± 1.33 | 2.53 ± 1.36 | 2.45 ± 1.43 | 1.33 ± 1.15 | 2.38 ± 1.38 |
| | | M + F | 1.67 ± 1.41 | 2.17 ± 1.50 | 2.50 ± 1.40 | 1.33 ± 1.15 | 2.23 ± 1.43 |
| | Severity | M | 1.00 ± 1.00 | 0.33 ± 0.58 | 2.33 ± 0.58 | — | 1.22 ± 1.09 |
| | | F | 1.83 ± 1.17 | 1.81 ± 1.17 | 2.16 ± 1.32 | 1.00 ± 1.00 | 1.96 ± 1.25 |
| | | M + F | 1.56 ± 1.13 | 1.58 ± 1.22 | 2.18 ± 1.27 | 1.00 ± 1.00 | 1.86 ± 1.25 |

TABLE 1-continued

Gastroparesis Cardinal Symptom Index (GCSI) survey response summary*

| GCSI Symptom | Descriptors | Sex | Type 1 Diab. | Type 2 Diab. | Idiopathic | Postsurgical | Combined |
|---|---|---|---|---|---|---|---|
| Epigastric Pain | Frequency | M | 0.33 ± 0.58 | 0.67 ± 1.15 | 1.75 ± 2.06 | — | 1.00 ± 1.49 |
| | | F | 1.33 ± 1.63 | 1.53 ± 1.51 | 2.18 ± 1.38 | 2.33 ± 1.53 | 1.92 ± 1.45 |
| | | M + F | 1.00 ± 1.41 | 1.39 ± 1.46 | 2.13 ± 1.44 | 2.33 ± 1.53 | 1.78 ± 1.48 |
| | Severity | M | 0.33 ± 0.58 | 1.33 ± 2.31 | 1.50 ± 1.73 | — | 1.10 ± 1.60 |
| | | F | 1.00 ± 1.26 | 1.50 ± 1.51 | 2.00 ± 1.36 | 1.67 ± 0.58 | 1.73 ± 1.38 |
| | | M + F | 0.78 ± 1.09 | 1.47 ± 1.58 | 1.94 ± 1.39 | 1.67 ± 0.58 | 1.63 ± 1.42 |
| Epigastric Burn | Frequency | M | 0.00 ± 0.00 | 0.00 ± 0.00 | 1.25 ± 1.50 | — | 0.50 ± 1.08 |
| | | F | 1.67 ± 1.63 | 1.27 ± 1.33 | 1.50 ± 1.42 | 1.67 ± 1.53 | 1.46 ± 1.39 |
| | | M + F | 1.11 ± 1.54 | 1.06 ± 1.30 | 1.47 ± 1.41 | 1.67 ± 1.53 | 1.32 ± 1.39 |
| | Severity | M | 0.00 ± 0.00 | 0.00 ± 0.00 | 1.25 ± 1.50 | — | 0.50 ± 1.08 |
| | | F | 1.67 ± 1.37 | 1.06 ± 1.24 | 1.23 ± 1.20 | 1.67 ± 1.53 | 1.25 ± 1.22 |
| | | M + F | 1.11 ± 1.36 | 0.89 ± 1.20 | 1.23 ± 1.21 | 1.67 ± 1.53 | 1.14 ± 1.23 |
| Cardiac Pain | Frequency | M | 0.00 ± 0.00 | 0.33 ± 0.58 | 1.50 ± 1.73 | — | 0.70 ± 1.25 |
| | | F | 1.00 ± 0.63 | 1.20 ± 1.52 | 1.10 ± 1.42 | 1.00 ± 1.00 | 1.11 ± 1.34 |
| | | M + F | 0.67 ± 0.71 | 1.06 ± 1.43 | 1.14 ± 1.44 | 1.00 ± 1.00 | 1.05 ± 1.33 |
| | Severity | M | 0.00 ± 0.00 | 0.67 ± 1.15 | 1.25 ± 1.26 | — | 0.70 ± 1.06 |
| | | F | 1.00 ± 0.63 | 1.13 ± 1.45 | 0.97 ± 1.30 | 0.67 ± 0.58 | 1.00 ± 1.25 |
| | | M + F | 0.67 ± 0.71 | 1.05 ± 1.39 | 1.00 ± 1.28 | 0.67 ± 0.58 | 0.95 ± 1.22 |
| Cardiac Burn | Frequency | M | 0.00 ± 0.00 | 0.33 ± 0.58 | 1.25 ± 1.50 | — | 0.60 ± 1.07 |
| | | F | 1.00 ± 1.26 | 1.13 ± 1.60 | 1.03 ± 1.56 | 1.33 ± 1.53 | 1.07 ± 1.50 |
| | | M + F | 0.67 ± 1.12 | 1.00 ± 1.50 | 1.06 ± 1.54 | 1.33 ± 1.53 | 1.00 ± 1.45 |
| | Severity | M | 0.00 ± 0.00 | 0.33 ± 0.58 | 1.25 ± 1.50 | — | 0.60 ± 1.07 |
| | | F | 1.00 ± 1.26 | 1.00 ± 1.32 | 0.84 ± 1.39 | 1.00 ± 1.00 | 0.91 ± 1.31 |
| | | M + F | 0.67 ± 1.12 | 0.89 ± 1.24 | 0.89 ± 1.39 | 1.00 ± 1.00 | 0.86 ± 1.28 |

Data presented in Table 1 is reported as mean ± standard deviation.

Data presented in Table 1 is reported as mean±standard deviation.

To establish a relationship between stimulus parameters, vagal CNAP features and symptom scores, first a high-level regression analysis was performed to determine whether A) stimulus pulse current/charge predicted changes in total symptom score (the sum of all severity and frequency scores for all 9 symptoms on the GCSI survey) and/or whether B) the degree of vagal recruitment (i.e., the sum of left and right vagal CNAP volleys in the mean left and right CANP responses whose peaks are significantly different from 0 V at α=0.05) predicted changes in the total symptom score. The degree of vagal recruitment was computed as the sum of the eight binary values assigned to the mean left and right vagal CNAP responses, respectively. If no significant volleys were detected in either the left or right vagal response, then the number of significant CNAP volleys was equal to 0. Similarly, if only left vagal Aγ and B fiber volleys were detected, along with right vagal B fiber volleys, then the number of significant CNAP volleys was equal to: $LV_{A\beta}^{(-)}+LV_{A\gamma}^{(+)}+LV_{A\delta}^{(-)}+LV_{B}^{(+)}+RV_{A\beta}^{(-)}+RV_{A\gamma}^{(-)}+RV_{A\delta}^{(-)}+RV_{B}^{(+)}$ which is equal to 0+1+0+1+0+0+0+1=3.

Figure 4A:
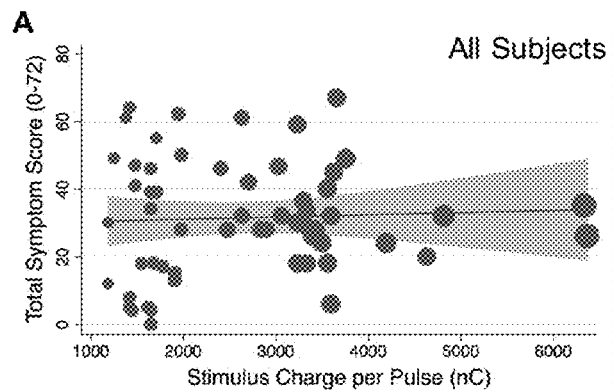
FIG. 4A is a plot that show total symptom score versus stimulus charge per pulse (in nC) for all (N=66) subjects.
Figure 4B:
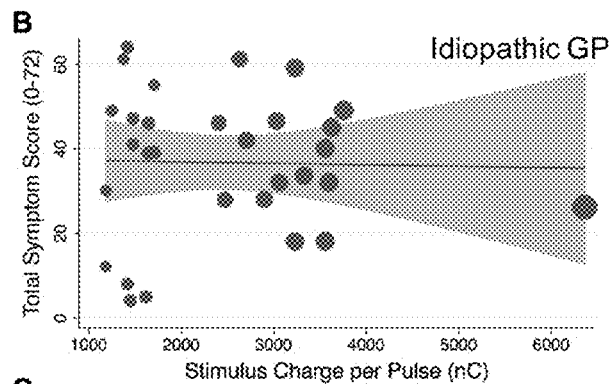
FIG. 4B shows results for 35 subjects with idiopathic gastroparesis.
Figure 4C:
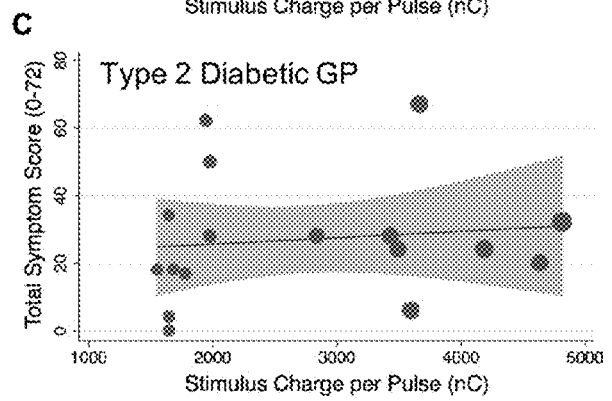
FIG. 4C shows results for the 19 subjects with type 2 diabetic gastroparesis.
Figure 4D:
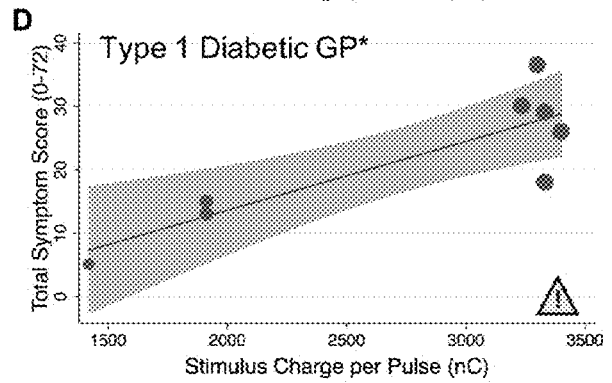
FIG. 4D shows results for the 9 subjects with type 1 diabetic gastroparesis.
Figure 4E:
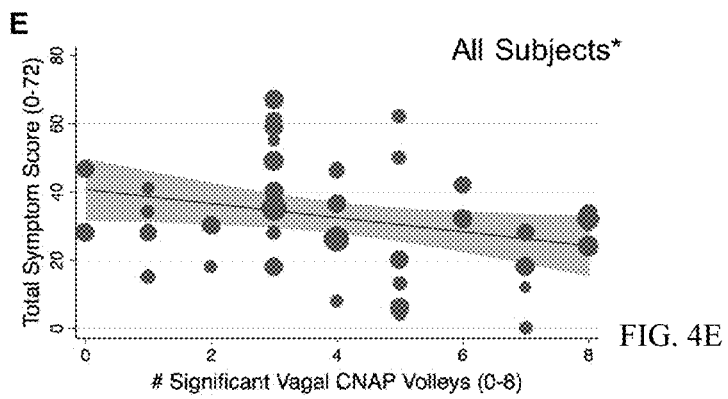
FIGS. 4E, 4F, 4G, and 4H show total symptom score versus the total number of significant CNAP volleys from the left and right vagal recordings (0-8) for all 66 subjects (FIG. 4E)
Figure 4F:
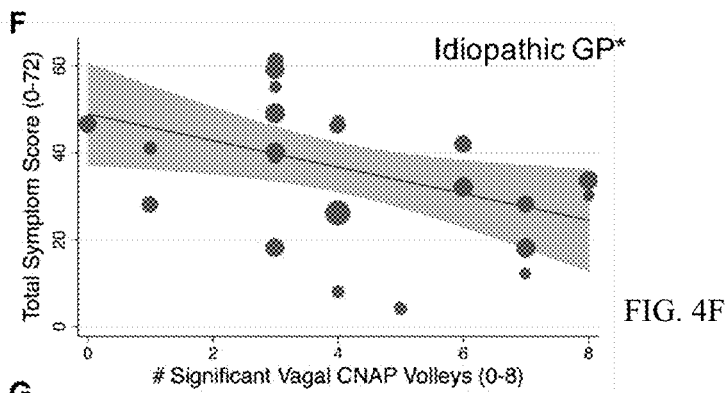
Figure 4G:
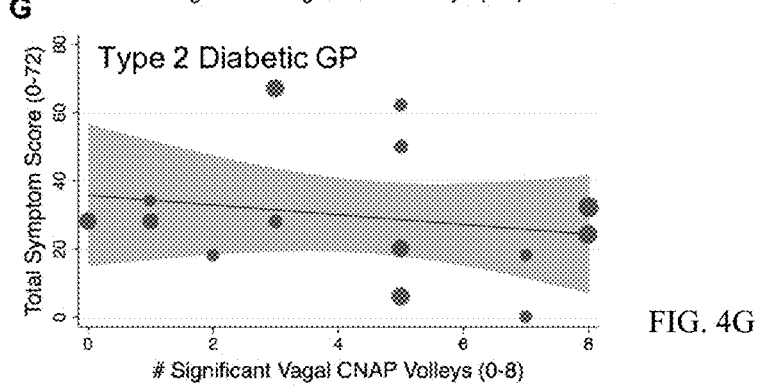
Figure 4H:
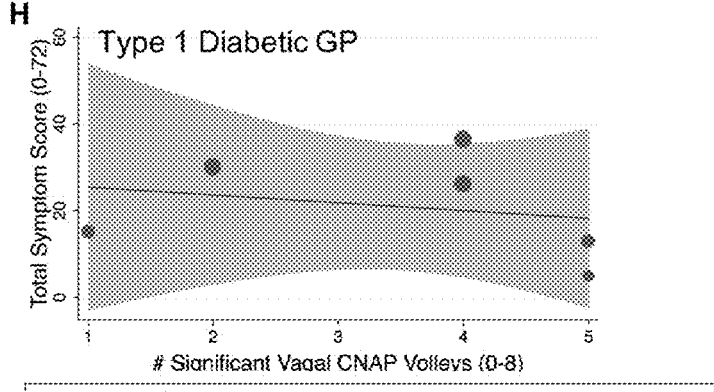

Stimulus pulse current and charge per pulse did not predict total symptom scores [F(1,56)=0.11; Prob>F=0.737]. Reference is made to FIGS. 4A-4G which show effects of stimulus strength and fiber recruitment on total GCSI symptom score. A regression analysis was performed to determine if stimulus charge per pulse and/or fiber recruitment number predict improvements in total GCSI symptom scores. FIGS. 4A-4D as plots that show total symptom score versus stimulus charge per pulse (in nC) for all (N=66) subjects. In particular, FIG. 4A shows all subjects; FIG. 4B results for shows 35 subjects with idiopathic gastroparesis; FIG. 4C shows results for the 19 subjects with type 2 diabetic gastroparesis; and FIG. 4D shows results for the 9 subjects with type 1 diabetic gastroparesis. Increasing stimulus charge per pulse predicted a higher total symptom score in type 1 diabetics (p<0.01), suggesting a worsening of their condition rather than an improvement as more energy is delivered. FIGS. 4E-4H show total symptom score versus the total number of significant CNAP volleys from the left and right vagal recordings (0-8) for all 66 subjects (see FIG. 4E); FIG. 4F shows results for the 35 subjects with idiopathic gastroparesis; FIG. 4G shows results for the 19 subjects with type 2 diabetic gastroparesis; and FIG. 4H shows results for the 9 subjects with type 1 diabetic gastroparesis. Increasing the number of significant CNAP volleys predicted a significant decrease in total symptom score for all subjects (E) (*p<0.05) and for subjects with idiopathic gastroparesis (F)(*p<0.05), suggesting an improvement in their condition with greater recruitment of the vagus. The warning/caution icon highlights a potential side effect of stimulation observed among type 1 diabetic subjects, inferred from a statistically significant increase in symptom score with increasing stimulus intensity, even when accounting for biological sex. There was a significant relationship between total number of significant left and right vagal CNAP volleys and total symptom score. As the total number of significant left and right vagal CNAP volleys increased, the observed total symptom score decreased [F(1,49)=4.68; Prob>F=0.035] (see FIG. 4E). When accounting for biological sex, the trend remains, but not the statistical significance for males [F(1,6)=0.93; Prob>F=0.373] or females [F(1,41)= 1.98; Prob>F=0.167].

Considering disease etiology, increasing stimulus charge per pulse predicted an increase (i.e., worsening) in total symptom score for type 1 diabetic subjects [F(1,6)=16.39; Prob>F=0.0067] (see FIG. 4D), but did not predict any change for subjects with idiopathic [F(1,28)=0.02; Prob>F=0.90] (see FIG. 4B) or type 2 diabetic gastroparesis [F(1,15)=0.22; Prob>F=0.648] (see FIG. 4C). When accounting for biological sex and disease etiology, a significant predictive relationship was no longer observed between stimulus charge per pulse and total symptom score for male [F(1,1)=5.46; Prob>F=0.257] or female[F(1,3)=7.60; Prob>F=0.070] subjects with type 1 diabetes.

As the total number of significant vagal CNAP volleys increased, there was an associated and significant decrease in total symptom score in subjects with idiopathic gastroparesis [$F(1,25)=6.04$; Prob>F=0.021] (FIG. 4F). When accounting for biological sex and disease etiology, the same significant trend remained for male [$F(1,1)=456.33$; Prob>F=0.030] and female [$F(1,22)=5.26$; Prob>F=0.032] subjects with idiopathic gastroparesis; note, however, that there were only three males with idiopathic gastroparesis in this study. No relationship was observed when performing the same analysis on subjects with type 2 [$F(1,13)=0.62$; Prob>F=0.446] (see FIG. 4G) or type 1 diabetic gastroparesis [$F(1,4)=0.26$; Prob>F=0.634] (see FIG. 4H).

Figure 5:
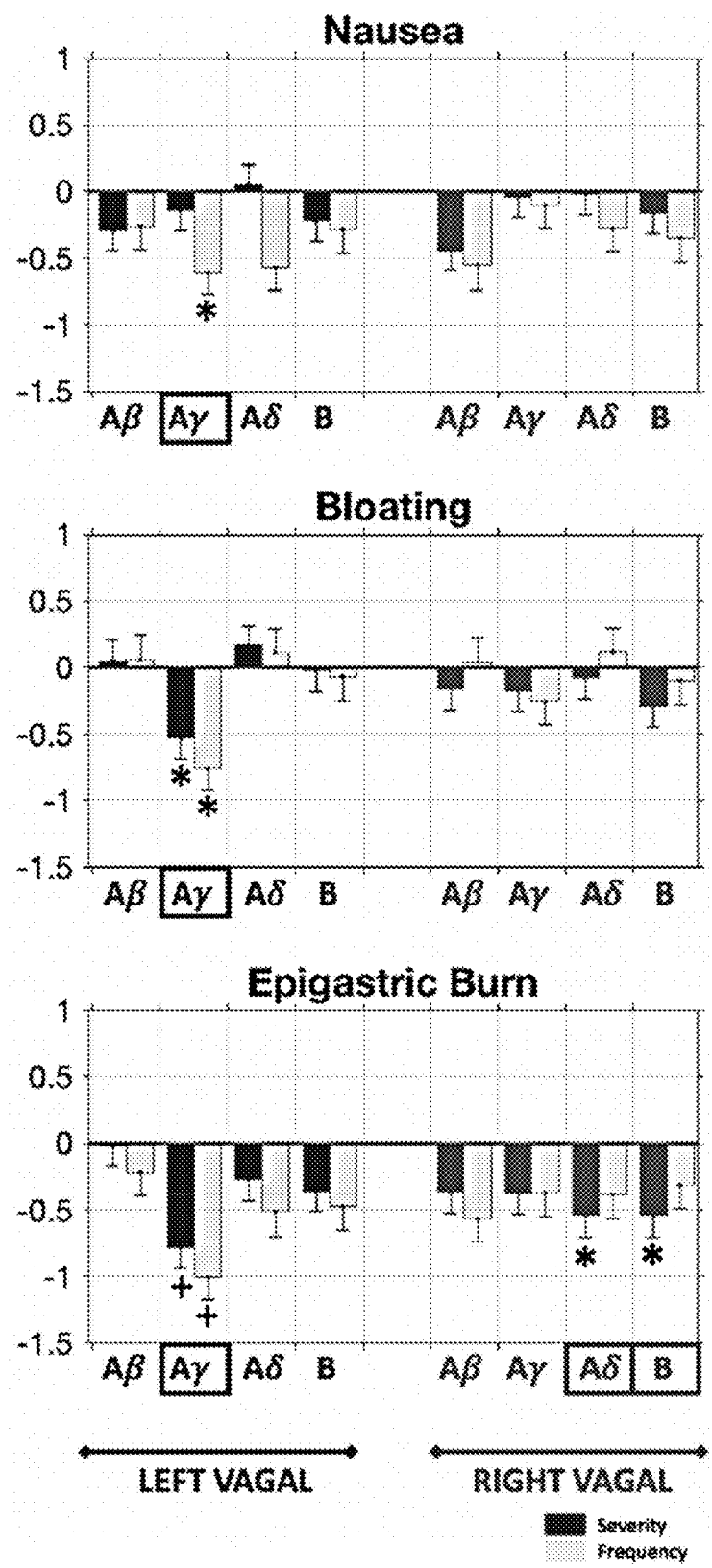
FIG. 5 (provided in three continuous pages) are plots which show the output of an analysis showing the difference in symptom severity and frequency scores from subjects whose recordings showed the presence of a particular fiber group [CNAP(+)] versus subjects whose recordings did not show the same response [CNAP(−)], without considering disease etiology, where the net difference in scores are reported as Gastroparesis Cardinal Symptom Index (GCSI) scale points (i.e., a scale of 0-4).
Figure 5:
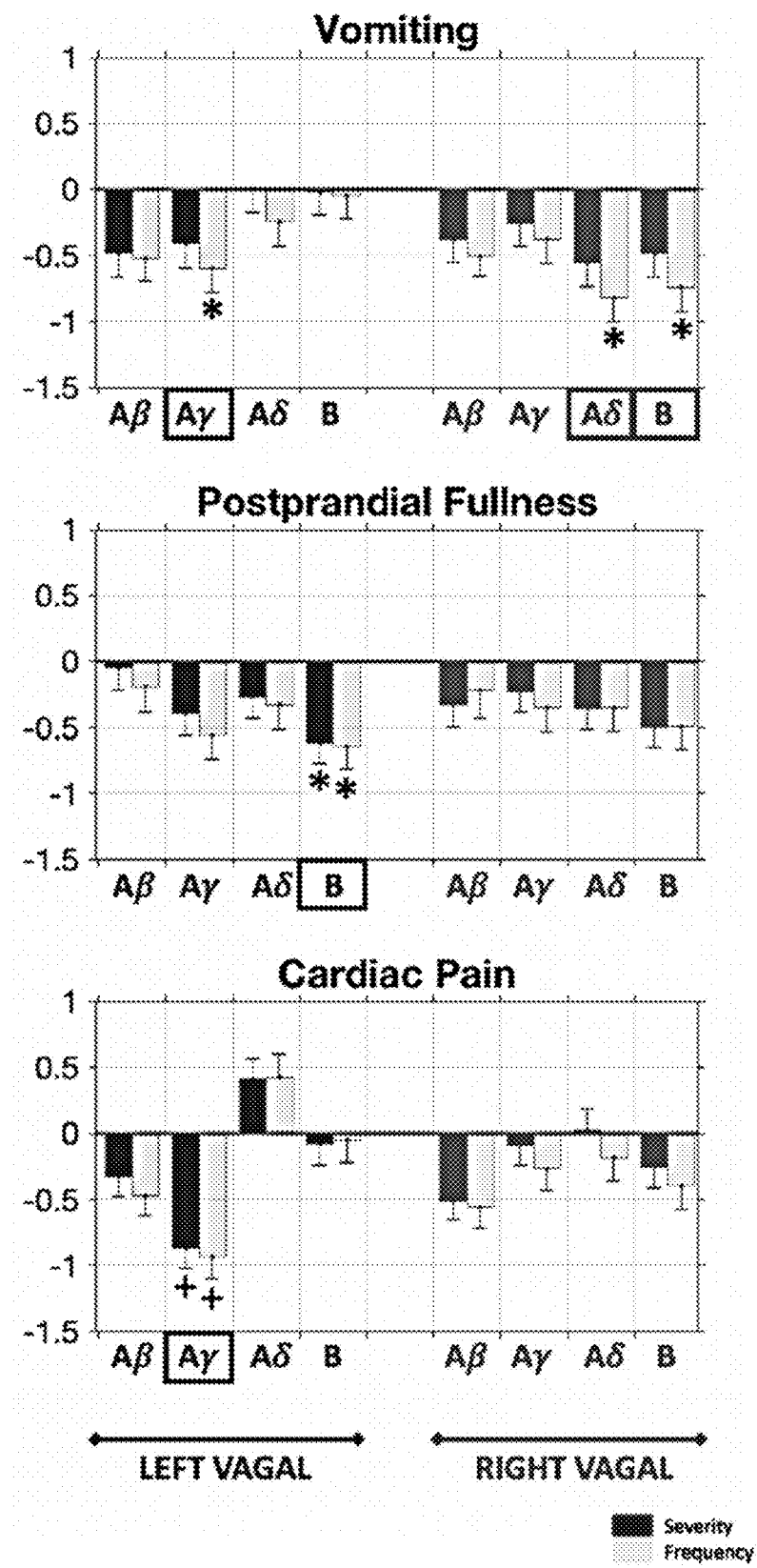
Figure 5:
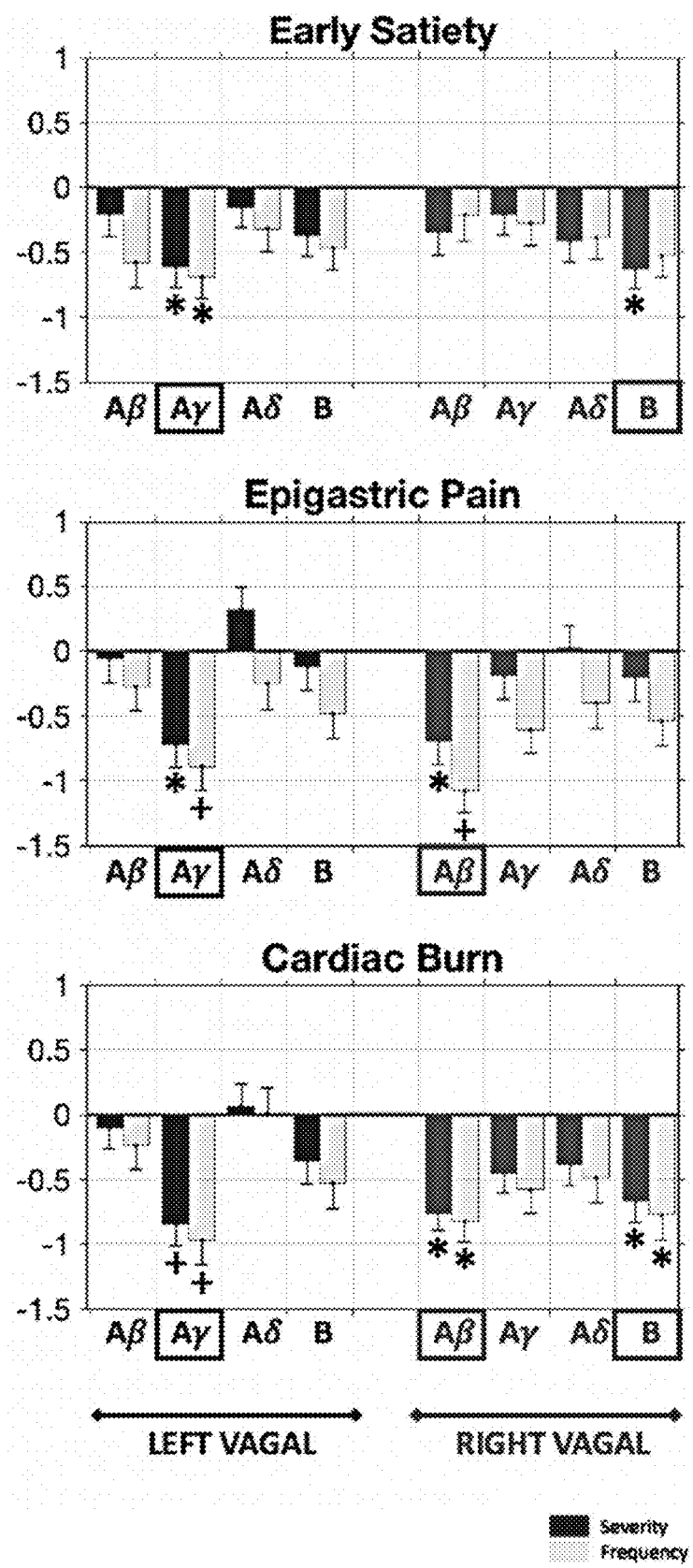

To determine more precisely whether specific fiber groups correlated with positive or negative changes in specific symptoms, the difference in symptom severity was computed and frequency scores from subjects whose recordings showed the presence of a particular fiber group [CNAP(+)] versus subjects whose recordings did not show the same response [CNAP(−)]. Referring to FIG. 5 (provided in three continuous pages) plots are presented which show the output of this analysis without considering disease etiology, where the net difference in scores are reported as GCSI scale points (i.e., a scale of 0-4). Note how the difference in symptom score was almost always negative using this analysis, which strongly suggested that the vagus was involved in mediating the therapeutic effects of GES therapy. Upon further inspection, it was clear that left vagal Aγ and B fibers, along with right vagal Aβ, Aδ and B fibers, played an important role in the mechanism of action of GES therapy, especially left vagal Aγ fibers.

Figure 6:
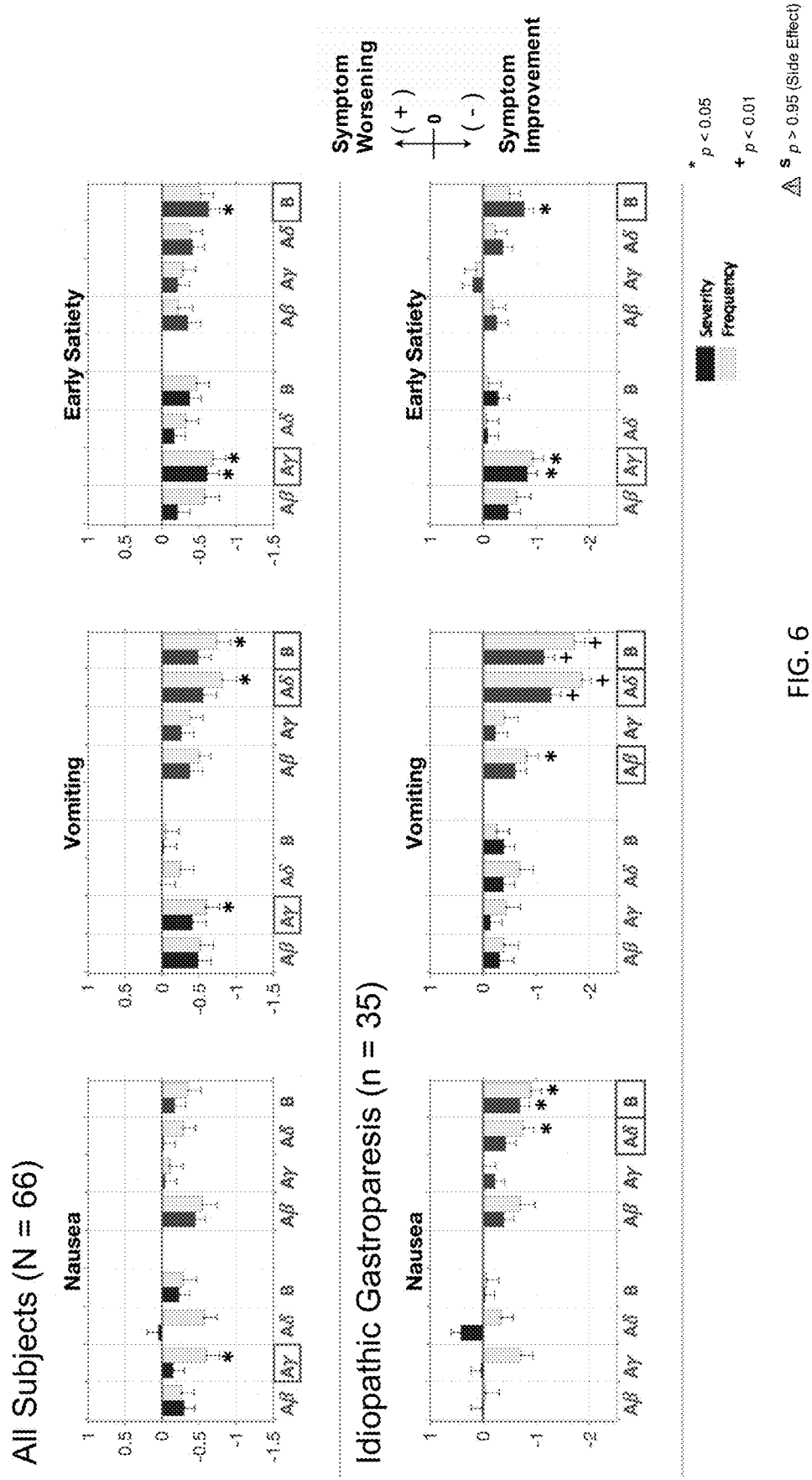
FIG. 6 (provided over two consecutive pages), are plots which show the output of an analysis considering disease etiology performed separately for nausea, vomiting and early satiety.
Figure 6:
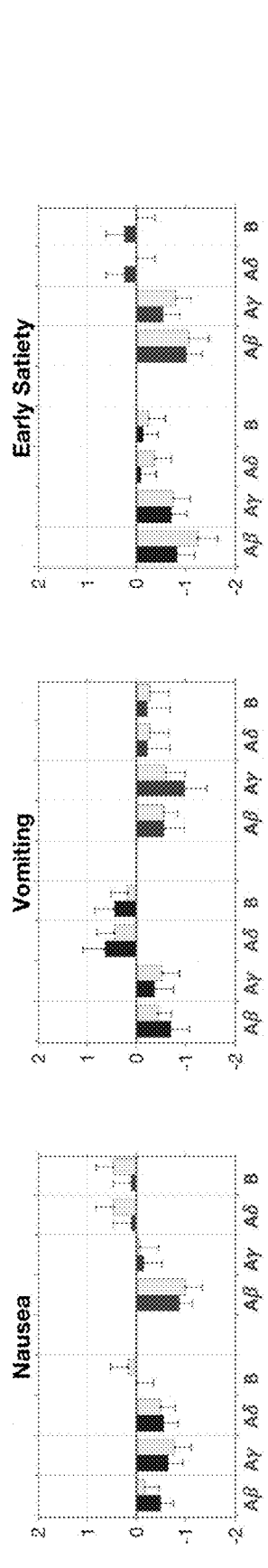
Figure 6:
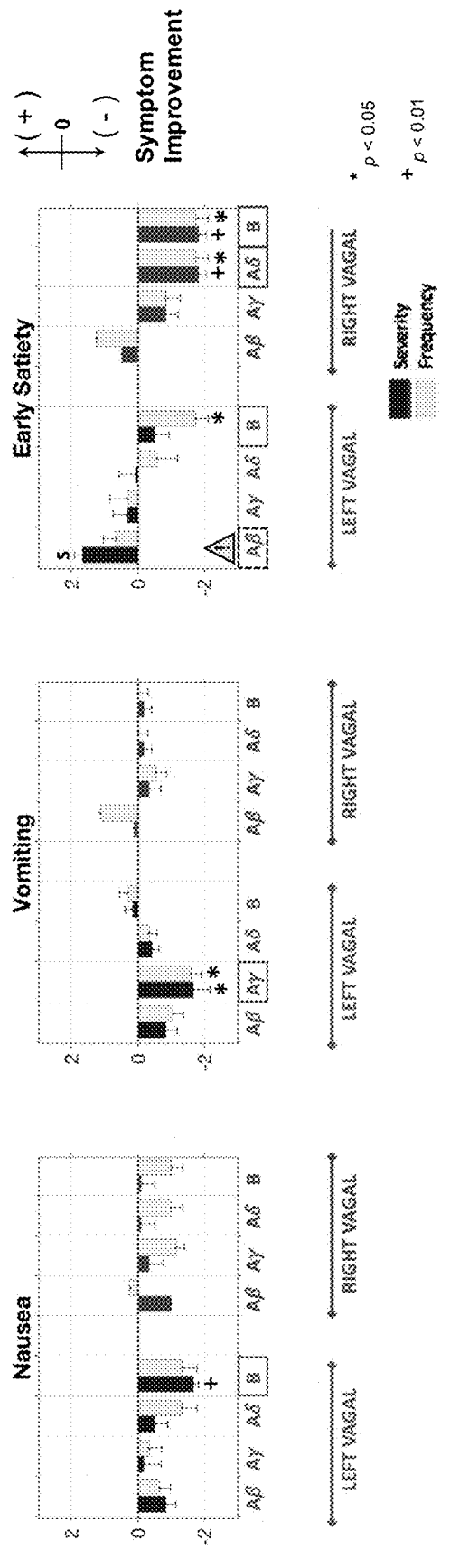

A similar analysis was performed separately for nausea, vomiting and early satiety, according to disease etiology, for which the results are shown in FIG. 6 (provided over two consecutive pages), which presents plots which show the output of this analysis considering disease etiology. In FIG. 6, a comparison of the output of the analysis of the effect of fiber activation on nausea, vomiting and early satiety symptom scores is provided. Of note, the analysis showed that the type of vagal recruitment associated with symptom improvement differed according to etiology.

For subjects with idiopathic gastroparesis, left vagal Aγ fiber recruitment predicted a significant improvement in the severity and frequency of early satiety ($p<0.05$, respectively). Right vagal Aβ fiber recruitment predicted a significant improvement in vomiting frequency ($p<0.05$). Right vagal Aδ fiber recruitment predicted significant improvements in nausea frequency ($p<0.05$), vomiting severity ($p<0.01$) and vomiting frequency ($p<0.01$). Right vagal B fiber recruitment predicted significant improvements in nausea severity and frequency ($p<0.05$), vomiting severity and frequency ($p<0.01$), and early satiety severity ($p<0.05$).

For subjects with type 2 diabetic gastroparesis, fiber recruitment did not predict any significant improvement in nausea, vomiting or early satiety symptoms. In contrast: For type 1 diabetics, left vagal Aβ fiber recruitment predicted a significant increase (i.e., worsening) in the severity of early satiety symptoms ($p>0.95$). This represented a potential side effect of GES therapy, consistent with the regression analysis that showed a significant increase in total symptom score as the energy delivered by the GES device increased. There was some potential benefit for type 1 diabetics, despite these apparent side effects: Left vagal Aγ fiber recruitment predicted a significant improvement in vomiting severity and frequency ($p<0.05$). Left vagal B fiber recruitment predicted a significant improvement in nausea severity ($p<0.01$) and early satiety frequency ($p<0.05$). Right vagal Aδ and B fiber recruitment predicted a significant improvement in early satiety severity ($p<0.01$) and frequency ($p<0.05$).

Cohen's d (an approach to measure differences between two averages, known to a person having ordinary skill in the art) was next used as a standardized metric to estimate the size of the symptom-reducing effect attributed to particular types of vagal nerve responses (representing an unbiased measure of the difference in mean values of subjects with or without a particular vagal response signature associated with their GES stimulus parameters). Any value greater than 0.8 is considered a large effect size. Any Cohen's d estimate whose 95% confidence interval does not include 0 is statistically significant. In Table 2, the output of the Cohen's d analysis performed in STATA 14 is shown to compare differences in the severity and frequency of the 9 hallmark symptoms of gastroparesis with or without the candidate "optimal" vagal response signature. Similar tables for idiopathic, type 2 and 1 diabetic gastroparesis are shown in Tables 3-5, respectively. Using this analysis, it was determined that left vagal Aγ along with right vagal Aδ and B fibers were critical components of the treatment response to GES. When absent, subjects consistently reported higher (i.e., worse) symptom scores.

TABLE 2

Effect of GES-evoked vagal signatures on symptom improvement (Cohen's d analysis)*

| | Vagal Fibers Linked to GES Efficacy | | | | | | | | Effect Size | Effect Size |
|---|---|---|---|---|---|---|---|---|---|---|
| | LEFT VAGUS | | | | RIGHT VAGUS | | | | (Cohen's d) | (Cohen's d) |
| GCSI Symptom | Aβ | Aγ | Aδ | B | Aβ | Aγ | Aδ | B | Symptom Severity | Symptom Frequency |
| Nausea | | ● | | | | | | | 0.12 [−0.38, 0.62] | 0.46 [−0.06, 0.97] |
| Vomiting | | ● | | | | | ● | ● | 0.86 [0.04, 1.65] | 1.18 [0.28, 2.06] |
| Early Satiety | | ● | | | | | | ● | 0.97 [0.16, 116] | 0.83 [0.05, 1.60] |
| Bloating | | ● | | | | | | | 0.44 [−0.06, 0.95] | 0.57 [0.06, 1.09] |
| Fullness | | | ● | | | | | | 0.51 [−0.01, 1.02] | 0.46 [−0.06, 0.97] |
| Epigastric Pain | | ● | | | ● | | | | 0.82 [0.10, 133] | 1.33 [0.55, 2.09] |
| Epigastric Burn | | ● | | | | | ● | ● | 1.23 [0.34, 2.08] | 1.11 [0.26, 1.93] |
| Cardiac Pain | | ● | | | | | | | 0.76 [0.23, 1.27] | 0.74 [0.21, 1.26] |
| Cardiac Burn | | ● | ● | | | | | ● | 1.63 [0.46, 2.75] | 1.74 [0.53, 2.89] |

TABLE 3

Summary of study population characteristics and GES device settings*

|  | Sex | Type 1 Diab. | Type 2 Diab. | Idiopathic | Postsurgical | Combined |
|---|---|---|---|---|---|---|
| # Subjects | M | 3 | 3 | 4 | 0 | 10 |
|  | F | 6 | 16 | 31 | 3 | 56 |
|  | M + F | 9 | 19 | 35 | 3 | 66 |
| Age (yr.) | M | 53.7 ± 15.9 | 49.0 ± 27.5 | 34.8 ± 11.6 | — | 44.7 ± 18.6 |
|  | F | 48.7 ± 8.00 | 52.3 ± 10.5 | 46.5 ± 10.4 | 57.7 ± 10.1 | 49.0 ± 10.4 |
|  | M + F | 50.3 ± 10.5 | 51.8 ± 13.3 | 45.1 ± 11.0 | 57.7 ± 10.1 | 48.3 ± 11.9 |
| BMI (kg/m^2) | M | 21.6 ± 2.10 | 31.9 ± 10.7 | 20.6 ± 3.10 | — | 24.3 ± 7.60 |
|  | F | 28.6 ± 7.40 | 30.0 ± 8.60 | 27.5 ± 5.60 | 31.1 ± 14.6 | 28.5 ± 7.20 |
|  | M + F | 26.3 ± 6.90 | 30.3 ± 8.70 | 26.7 ± 5.70 | 31.1 ± 14.6 | 27.9 ± 7.30 |
| GES Electrode Resistance (Ω) | M | 551. ± 72.4 | 534. ± 50.6 | 514. ± 74.8 | — | 531. ± 62.2 |
|  | F | 541. ± 75.0 | 570. ± 97.4 | 566. ± 105. | 588. ± 124. | 566. ± 99.0 |
|  | M + F | 545. ± 69.6 | 564. ± 91.5 | 560. ± 103. | 588. ± 124. | 561. ± 94.8 |
| Stimulus Pulse Voltage (V) | M | 3.77 ± 2.02 | 4.67 ± 1.47 | 3.83 ± 0.83 | — | 4.06 ± 1.34 |
|  | F | 4.72 ± 1.30 | 4.34 ± 1.51 | 3.98 ± 1.56 | 7.30 ± 1.81 | 4.34 ± 1.67 |
|  | M + F | 4.40 ± 1.52 | 4.39 ± 1.47 | 3.97 ± 1.48 | 7.30 ± 1.81 | 4.30 ± 1.62 |
| Stimulus Pulse Current (mA) | M | 6.74 ± 3.01 | 8.83 ± 3.32 | 7.68 ± 2.41 | — | 7.74 ± 2.67 |
|  | F | 8.67 ± 2.15 | 7.88 ± 3.30 | 7.18 ± 3.55 | 11.6 ± 6.62 | 7.78 ± 3.60 |
|  | M + F | 8.03 ± 2.47 | 8.03 ± 3.23 | 7.24 ± 3.42 | 11.6 ± 6.62 | 7.77 ± 3.46 |
| Stimulus Pulse Duration (µs) | M | 330. ± 0.00 | 330. ± 0.00 | 330. ± 0.00 | — | 330. ± 0.00 |
|  | F | 330. ± 0.00 | 338. ± 30.0 | 334. ± 21.6 | 330. ± 0.00 | 334. ± 22.5 |
|  | M + F | 330. ± 0.00 | 336. ± 27.5 | 333. ± 20.3 | 330. ± 0.00 | 334. ± 20.7 |
| Stimulus Frequency (Hz) | M | 27.7 ± 23.7 | 32.3 ± 20.8 | 34.5 ± 23.7 | — | 31.8 ± 20.4 |
|  | F | 30.0 ± 20.1 | 14.1 ± 0.50 | 14.1 ± 0.40 | 14.0 ± 0.00 | 15.8 ± 7.80 |
|  | M + F | 29.2 ± 19.9 | 17.0 ± 9.75 | 16.4 ± 9.65 | 14.0 ± 0.00 | 18.2 ± 12.0 |
| Stimulus ON Time (s) | M | 0.40 ± 0.51 [0.1 1.0] | 0.10 ± 0.00 [0.1 0.1] | 0.33 ± 0.45 [0.1 1.0] | — | 0.28 ± 0.38 [0.1 1.0] |
|  | F | 0.42 ± 0.78 [0.1 2.0] | 0.33 ± 0.54 [0.01 2.0] | 0.17 ± 0.23 [0.1 1.0] | 0.73 ± 1.10 [0.1 2.0] | 0.27 ± 0.48 [0.01 2.0] |
|  | M + F | 0.41 ± 0.67 [0.1 2.0] | 0.30 ± 0.50 [0.01 2.0] | 0.19 ± 0.26 [0.1 1.0] | 0.73 ± 1.10 [0.1 2.0] | 0.27 ± 0.46 [0.01 2.0] |
| Stimulus OFF Time (s) | M | 4.27 ± 1.10 [3.0 4.9] | 5.00 ± 0.00 [5.0 5.0] | 4.68 ± 0.45 [4.0 4.9] | — | 4.65 ± 0.65 [3.0 5.0] |
|  | F | 4.33 ± 1.63 [1.0 5.0] | 4.77 ± 0.53 [3.0 5.0] | 4.89 ± 0.24 [4.0 5.0] | 4.33 ± 1.15 [3.0 5.0] | 4.77 ± 0.66 [1.05.0] |
|  | M + F | 4.31 ± 1.40 [1.0 5.0] | 4.81 ± 0.49 [3.0 5.0] | 4.86 ± 0.27 [4.0 5.0] | 4.33 ± 1.15 [3.0 5.0] | 4.75 ± 0.66 [1.0 5.0] |

TABLE 4

Effect of GES-evoked vagal signatures on symptom improvement n = 35 subjects with idiopathic gastroparesis (Cohen's d analysis)*

| GCSI Symptom | Vagal Fibers Linked to GES Efficacy | | | | | | | | Effect Size (Cohen's d) Symptom Severity | Effect Size (Cohen's d) Symptom Frequency |
|---|---|---|---|---|---|---|---|---|---|---|
|  | LEFT VAGUS | | | | RIGHT VAGUS | | | | | |
|  | Aβ | Aγ | Aδ | B | Aβ | Aγ | Aδ | B | | |
| Nausea |  |  |  |  |  |  | ●. | ● | 0.71 [−0.04, 1.45] | 0.71 [−0.10, 1.50] |
| Vomiting |  |  |  |  |  | ●. |  | ● | 1.22 [0.38, 2.03] | 2.65 [1.24, 4.02] |
| Early Satiety |  | ● |  |  |  |  | ●. |  | 1.21 [0.08, 2.31] | 0.78 [0.06, 1.49] |
| Bloating |  |  |  |  |  |  |  |  | No observed effect | No observed effect |
| Fullness |  |  | ● |  |  |  |  |  | 0.76 [0.05, 1.46] | 0.54 [−0.15, 1.24] |
| Epigastric Pain | ● |  | ● | ● |  |  |  | ● | 0.60 [−1.17, 2.26] | 2.31 [−0.53, 5.07] |
| Epigastric Burn | ● | ●. | ● |  |  |  | ● | ●. | 4.65 [0.59, 8.88] | 3.87 [−0.35, 8.50] |
| Cardiac Pain | ● |  |  |  |  |  |  |  | 0.87 [0.12, 1.60] | 0.99 [0.22, 1.73] |
| Cardiac Burn | ● |  | ● |  | ● |  |  | ● | 6.36 [−0.26, 14.37] | 14.85 [0.27, 33.33] |

TABLE 5

Effect of GES-evoked vagal signatures on symptom improvement n = 19 subjects with type 2 diabetic gastroparesis (Cohen's d analysis)*

| | Vagal Fibers Linked to GES Efficacy | | | | | | | | Effect Size | Effect Size |
|---|---|---|---|---|---|---|---|---|---|---|
| | LEFT VAGUS | | | | RIGHT VAGUS | | | | (Cohen's d) | (Cohen's d) |
| GCSI Symptom | Aβ | Aγ | Aδ | B | Aβ | Aγ | Aδ | B | Symptom Severity | Symptom Frequency |
| Nausea | | | | | | | | | No observed effect | No observed effect |
| Vomiting | | | | | | | | | No observed effect | No observed effect |
| Early Satiety | | | | | | | | | No observed effect | No observed effect |
| Bloating | | | | | | | | | No observed effect | No observed effect |
| Fullness | | | | | | | | | No observed effect | No observed effect |
| Epigastric Pain | | | | | | | ● | | 0.47 [−0.55, 1.47] | 0.84 [−0.23, 1.89] |
| Epigastric Burn | | | | | | | | | No observed effect | No observed effect |
| Cardiac Pain | | | | | | ● | | | 0.89 [−0.17, 1.92] | 1.06 [−0.06, 2.15] |
| Cardiac Burn | | | | | | ● | | | 1.13 [0.03, 2.19] | 1.11 [−0.03, 2.20] |

*Cohen's d was used here as a metric to estimate the magnitude and relative significance of the symptom improvement (i.e., reduction in absolute GCSI symptom scores) to be expected when GES is tuned to produce particular types of vagal responses (shown in each row next to the symptom names).

*Cohen's d was used here as a metric to estimate the magnitude and relative significance of the symptom improvement (i.e., reduction in absolute GCSI symptom scores) to be expected when GES is tuned to produce particular types of vagal responses (shown in each row next to the symptom names).

Figure 7:
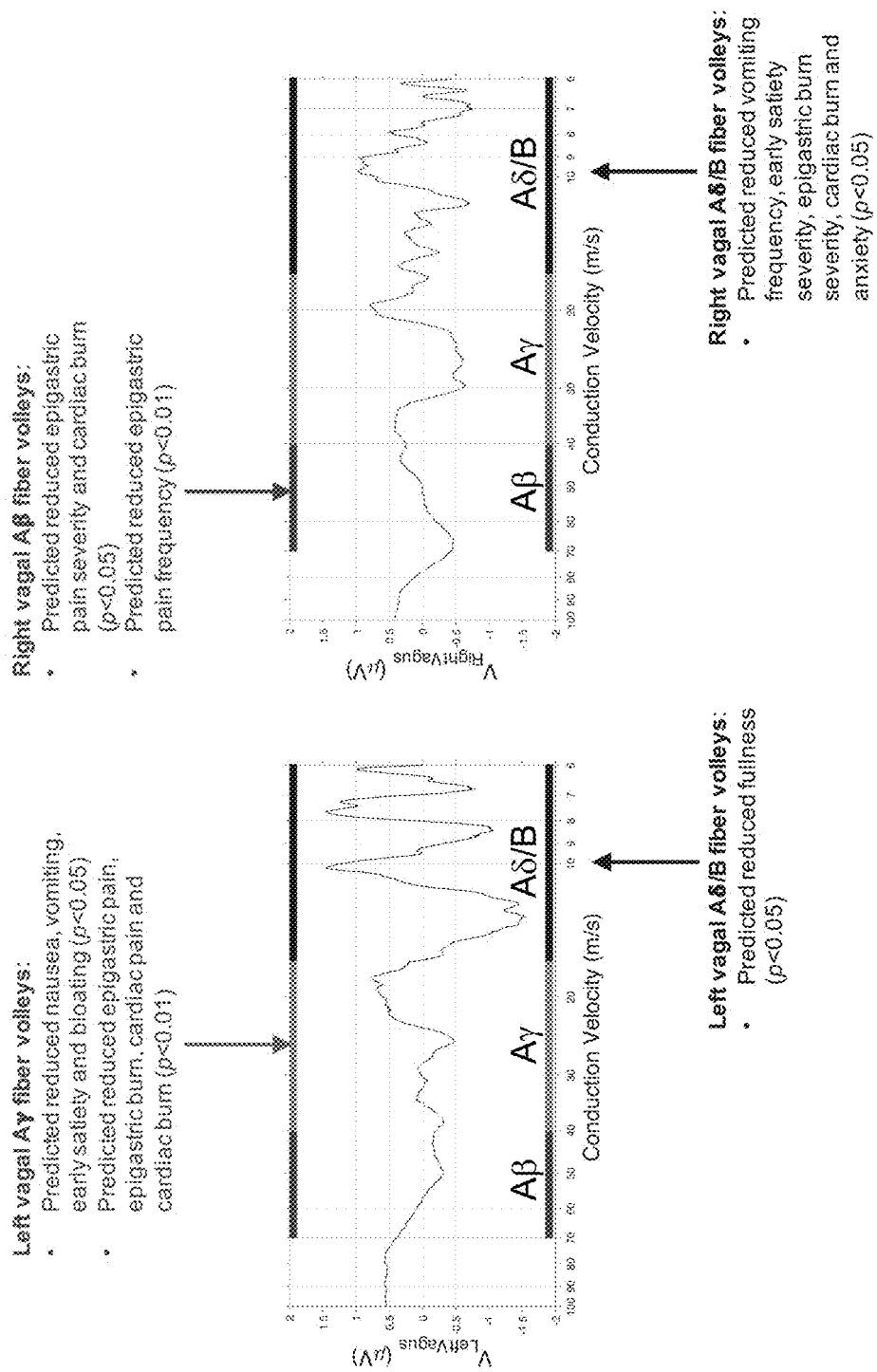
FIG. 7 are two plots of vagal sensor output in $\mu$V vs. conduction velocity in m/s which show a high level summary of the predicted nerve fiber population characteristics whose activity correlates with improvements in specific symptoms of gastroparesis.

Through the novel analytical methods presented herein, it has been shown that it is possible to extract meaningful information from the vagus nerve in response to gastric electrical stimulation using simple, but well-placed cutaneous electrodes, and a methodical, progressive method of data reduction for comparative analyses. Referring to FIG. 7, two plots are provided of vagal sensor output in μV vs. conduction velocity in m/s are presented which show a high level summary of the predicted nerve fiber population characteristics whose activity correlates with improvements in specific symptoms of gastroparesis. The data is plotted from one subject whose data showed significant fiber recruitment in all left and right vagal fiber groups considered in the analysis. The p-values refer to analyses performed with all N=66 subjects included in the study. It has been shown that stimulus parameters do not predict any change in symptom scores outside of predicting a substantial increase (i.e., worsening) in the total symptom score for type diabetics as the charge per stimulus pulse increases (p=0.0067). The charge per pulse can be treated as interchangeable with the stimulus pulse current in this particular study, because the stimulus pulse duration is almost always fixed at 330 μs. In contrast, there is a significant reduction in total symptom scores as the total number of classes of fibers (left plus right) that show significant signals when the gastric electrodes were activated increased (p=0.035). This same relationship held for subjects with idiopathic gastroparesis (p=0.021), but not for subjects with diabetic gastroparesis. Taken together, a conclusion can be drawn that the vagus is an essential component of the mechanism of action of GES therapy, especially for subjects with idiopathic or type 1 diabetic gastroparesis. The presence of side effects attributed to the activation of certain fiber groups in type 1 and 2 diabetic subjects underscores the utility of our approach and the need to develop feedback systems that can enable fine-tuning of the nerve response that predicts a positive therapeutic response to GES therapy in each subject even though the stimulus parameters required to recruit the desired nerve response will likely differ across subjects and perhaps within the same subjects over time.

Consequently, the present disclosure shows Vagal CNAP analysis is a useful technique to define relationships among GES parameters, vagal recruitment, efficacy and side-effect management. Our results show that CNAP-guided GES optimization provides benefit to patients with a variety of patient conditions including type 1 diabetic gastroparesis, especially when tuned for left vagal Aγ and right vagal Aδ/B fiber responses, which consistently predict symptom score improvements. The side effects associated with left vagal Aβ activation in type 1 diabetics underscore the need to consider disease etiology in the patient and parameter selection process.

Those having ordinary skill in the art will recognize that numerous modifications can be made to the specific implementations described above. The implementations should not be limited to the particular limitations described. Other implementations may be possible.

The invention claimed is:

1. A gastric electric stimulation system, comprising:
   a processing system having a processor; and
   at least one of a left vagus nerve sensor and a right vagus nerve sensor coupled to the processing system;
   the processing system configured to:
      receive a model which statistically correlates sensed compound nerve action potential (CNAP) parameters measured from at least one of left and right vagus nerves of subjects within a population to feedback surveys of the subjects in the population corresponding to a plurality of gastric symptoms and symptom parameters,
      receive one or more gastric symptoms of a subject outside of the population ($Subject_{out}$),
      from the model determine CNAP parameters that correspond to the gastric symptoms with least severity ($CNAP_{min}$),
      measure CNAP activity of the $Subject_{out}$ from the at least one of left and right vagus nerve sensors while modifying gastric electrical stimulation (GES) parameters for the $Subject_{out}$ from a plurality of predetermined GES parameters,
      select the GES parameters from the plurality of predetermined GES parameters that corresponds to the $CNAP_{min}$ ($GES_{out}$), and
      output the $GES_{out}$.

2. The system of claim 1, wherein the GES parameters include frequency, amplitude, and pulse width,
   wherein the frequency is selected from the group consisting of 14 Hz, 28 Hz, and 55 Hz,
   wherein the pulse width is selected from the group consisting of 210 µs, 330 µs, and 450 µs, and
   wherein the amplitude is selected from the group consisting of 2.5 mA, 5 mA, 7.5 mA, and 10 mA.

3. The system of claim 1, wherein the plurality of gastric symptoms are selected from the group consisting of nausea, vomiting, early satiety, bloating, fullness, epigastric pain, epigastric burn, cardiac pain, and cardiac burn.

4. The system of claim 1, wherein the symptom parameters of the plurality of gastric symptoms include severity, frequency, and duration,
   wherein severity is selected from the group consisting of 0, 1, 2, 3, or 4, wherein 0 refers to no symptom, and 4 refers to a highest severity for an associated symptom of the plurality of gastric symptoms, and
   wherein the CNAP parameters are selected from the group consisting of A$\beta$, A$\gamma$, and A$\delta$, B, and C.

5. The system of claim 1, wherein the model determines the CNAP parameters from raw vagal recordings by i) determining conduction velocity of each vagal nerve activity, ii) determining timestamp of each GES stimulus, iii) discriminating between the CNAP parameters using predetermined thresholds in between the GES stimuli, and iv) averaging the CNAP parameters,
   wherein the timestamp of each GES stimulus is determined based on electrocardiogram signals.

6. The system of claim 1, the processor is further configured to:
   convey response of the $Subject_{out}$ to the model, wherein the response includes vagal recording from the at least one of left and right vagus nerve sensors, timestamps associated with stimulation based on the $GES_{out}$, and a survey from the $Subject_{out}$ corresponding to the $GES_{out}$.

7. The system of claim 1, wherein the feedback surveys further include patient-related parameters and the model further discriminates based on the patient-related parameters of the subjects within the population,
   wherein the patient-related parameters include diseases, gender, race, and body mass index.

8. The system of claim 7, wherein the diseases are selected from the group consisting of type-I diabetes, type-II diabetes, post-surgical gastroparesis, and post-viral/bacterial gastroparesis.

9. The system of claim 6, wherein the response further includes patient-related parameters and the model further discriminates based on the patient-related parameters of $Subject_{out}$, wherein the patient-related parameters include diseases, gender, race, and body mass index.

10. The system of claim 9, wherein the diseases are selected from the group consisting of type-I diabetes, type-II diabetes, post-surgical gastroparesis, and post-viral/bacterial gastroparesis.

11. A method of gastric electric stimulation, comprising:
    receiving at least one of a left vagus nerve sensor output and a right vagus nerve sensor output;
    receiving a model which statistically correlates sensed compound nerve action potential (CNAP) parameters measured from at least one of left and right vagus nerves of subjects within a population to feedback surveys of the subjects in the population corresponding to a plurality of gastric symptoms and symptom parameters,
    receiving one or more gastric symptoms of a subject outside of the population ($Subject_{out}$),
    from the model determining CNAP parameters that correspond to the gastric symptoms with least severity ($CNAP_{min}$),
    measuring CNAP activity of the $Subject_{out}$ from the at least one of left and right vagus nerve sensors while modifying gastric electrical stimulation (GES) parameters for the $Subject_{out}$ from a plurality of predetermined GES parameters,
    selecting the GES parameters from the plurality of predetermined GES parameters that corresponds to the $CNAP_{min}$ ($GES_{out}$), and outputting the $GES_{out}$.

12. The method of claim 11, wherein the GES parameters include frequency, amplitude, and pulse width,
    wherein the frequency is selected from the group consisting of 14 Hz, 28 Hz, and 55 Hz,
    wherein the pulse width is selected from the group consisting of 210 µs, 330 µs, and 450 µs, and
    wherein the amplitude is selected from the group consisting of 2.5 mA, 5 mA, 7.5 mA, and 10 mA.

13. The method of claim 11, wherein the plurality of gastric symptoms are selected from the group consisting of nausea, vomiting, early satiety, bloating, fullness, epigastric pain, epigastric burn, cardiac pain, and cardiac burn.

14. The method of claim 11, wherein the symptom parameters of the plurality of gastric symptoms include severity, frequency, and duration,
    wherein severity is selected from the group consisting of 0, 1, 2, 3, or 4, wherein 0 refers to no symptom, and 4 refers to a highest severity for an associated symptom of the plurality of gastric symptoms, and
    wherein the CNAP parameters are selected from the group consisting of A$\beta$, A$\gamma$, and A$\delta$, B, and C.

15. The method of claim 11, wherein the model determines the CNAP parameters from raw vagal recordings by i) determining conduction velocity of each vagal nerve activity, ii) determining timestamp of each GES stimulus, iii) discriminating between the CNAP parameters using predetermined thresholds in between the GES stimuli, and iv) averaging the CNAP parameters,
    wherein the timestamp of each GES stimulus is determined based on electrocardiogram signals.

16. The method of claim 11, the processor is further configured to:
    convey response of the $Subject_{out}$ to the model, wherein the response includes vagal recording from the at least one of left and right vagus nerve sensors, timestamps associated with stimulation based on the $GES_{out}$, and a survey from the $Subject_{out}$ corresponding to the $GES_{out}$.

17. The method of claim 11, wherein the feedback surveys further include patient-related parameters and the model further discriminates based on the patient-related parameters of the subjects within the population,
    wherein the patient-related parameters include diseases, gender, race, and body mass index.

18. The method of claim 17, wherein the diseases are selected from the group consisting of type-I diabetes, type-II diabetes, post-surgical gastroparesis, and post-viral/bacterial gastroparesis.

19. The method of claim 16, wherein the response further includes patient-related parameters and the model further discriminates based on the patient-related parameters of $Subject_{out}$, wherein the patient-related parameters include diseases, gender, race, and body mass index.

20. The method of claim 19, wherein the diseases are selected from the group consisting of type-I diabetes, type-II diabetes, post-surgical gastroparesis, and post-viral/bacterial gastroparesis.

* * * * *